(12) United States Patent
Liu et al.

(10) Patent No.: US 11,923,082 B2
(45) Date of Patent: Mar. 5, 2024

(54) METHOD AND SYSTEM FOR RAPID PREDICTION OFFAST BLOOD GLUCOSE LEVEL IN PREGNANT SUBJECTS

(71) Applicants: Hangzhou Calibra Diagnostics Co., Ltd., Hangzhou (CN); Hangzhou Dian Medical Inspection Center Co., Ltd., Hangzhou (CN)

(72) Inventors: Huafen Liu, Hangzhou (CN); Ziqing Kong, Hangzhou (CN); Chao Zhang, Hangzhou (CN); Rongchang Chen, Hangzhou (CN); Yuning Zhu, Hangzhou (CN)

(73) Assignees: HANGZHOU CALIBRA DIAGNOSTICS CO., LTD., Hangzhou (CN); HANGZHOU DIAN MEDICAL INSPECTION CENTER CO., LTD., Hangzhou (CN)

( * ) Notice: Subject to any disclaimer, the term of this patent is extended or adjusted under 35 U.S.C. 154(b) by 0 days.

(21) Appl. No.: 17/837,442

(22) Filed: Jun. 10, 2022

(65) Prior Publication Data
US 2023/0307120 A1  Sep. 28, 2023

(30) Foreign Application Priority Data

Jan. 24, 2022  (CN) .......................... 202210083776.9
Jan. 24, 2022  (CN) .......................... 202210083970.7

(51) Int. Cl.
*G16H 40/63* (2018.01)
*G01N 33/68* (2006.01)

(52) U.S. Cl.
CPC ......... *G16H 40/63* (2018.01); *G01N 33/6851* (2013.01); *G01N 33/6893* (2013.01); *G01N 2800/042* (2013.01)

(58) Field of Classification Search
None
See application file for complete search history.

(56) References Cited

U.S. PATENT DOCUMENTS

2015/0024422 A1  1/2015  Pottala
2019/0285656 A1  9/2019  Jia

FOREIGN PATENT DOCUMENTS

| CN | 103403548 A | 11/2013 |
| CN | 103592389 A | 12/2014 |

(Continued)

OTHER PUBLICATIONS

Forrester, Alexander I.J. et al., "Engineering Design via Surrogate Modelling: A Practical Guide", John Wiley & Sons Ltd., Aviation Industry Press, Nov. 30, 2008, pp. 59-62.

(Continued)

*Primary Examiner* — Xiaoyun R Xu
(74) *Attorney, Agent, or Firm* — MUNCY, GEISSLER, OLDS & LOWE, PC

(57) ABSTRACT

The present invention relates to a system for predicting gestational diabetes mellitus (GDM) of pregnant individuals, wherein the system comprises an operation module, and the operation model comprises a support vector regression model, and the system is used to predict the plasma glucose levels at 1 hour and/or 2 hours of oral glucose tolerance test (OGTT) by using a support vector regression developed prediction model generated by substituting the concentration of the biomarkers in fasting blood samples of pregnant individuals. The present invention provides biomarkers and biomarker-based diagnostic models for differential diagnosis of gestational diabetes mellitus (GDM), which can be applied to diagnosis or prediction of GDM in early stage and are of great significance to the prevention or treatment of GDM.

5 Claims, 14 Drawing Sheets

(56) References Cited

FOREIGN PATENT DOCUMENTS

| | | |
|---|---|---|
| CN | 108352193 A | 7/2018 |
| CN | 108766578 A | 11/2018 |
| CN | 110808097 A | 2/2020 |
| CN | 110988165 A | 4/2020 |
| CN | 112461986 A | 3/2021 |
| CN | 112786204 A | 5/2021 |
| CN | 112461986 B | 6/2021 |
| CN | 112903885 A | 6/2021 |
| CN | 113012806 A | 6/2021 |
| CN | 113295793 A | 8/2021 |
| TW | 201217788 A | 5/2012 |
| WO | WO2020240543 A1 | 12/2020 |

OTHER PUBLICATIONS

Du Cheng-Hua, et al., "Contrastive Analysis on the Prediction of Blood Glucose Level Based on Support Vector Regression and Kernel Ridge Regression", Mathematics in Practice and Theory, vol. 50, No. 6, 132-139, Mar. 2020, China Academic Journal Electronic Publishing House.

Mao et al., *Metabolomics in gestational diabetes*. Cilinica Chimica Acta, 2017, Elsevier B.V., pp. 116-127.

Zhao et al., *Trimester-specific urinary metabolome alterations associated with gestational diabetes mellitus: A study in different pregnancy stages*. Chinese Chemical Letters, 2021, Elsevier B.V on behalf of Chinese Chemical Society and Institute of Materia Medica, Chinese Academy of Medical Sciences., 5 pages.

Zhao et al., *Association of altered serum acylcarnitine levels in early pregnancy and risk of gestational diabetes mellitus*, Science China, Science China Press and Springer-Vertag GmbH Germany, Jan. 2020, vol. 63 No. 1: 126-134.

Hameed et al., Altered Metabolome of Lipids and Amino Acids Species: A Source of Early Signature Biomarkers of T2DM, Journal of Clinical Medicine, 2020, 9, 2257, 46 pages.

Lowe Jr. et al., Maternal BMI and Glycemia Impact the Fetal Metabolome, Diabetes Care, vol. 40, Jul. 2017, p. 902-910.

Libert et al., *Metabolomic analysis of obesity, metabolic syndrome, and type 2 diabetes: amino acid and acylcarnitine levels change along a spectrum of metabolic wellness*, 2018, PeerJ, 23 pages.

Roy et al., *Risk of gestational diabetes mellitus in relation to plasma concentrations of amino acids and acylcarnitines: A nested case-control study*, Diabetes research and Clinical Practice, 2018, Elsevier B.V, p. 183-190.

Elshenawy et al., The Metabolomic Signature of the Placenta in Spontaneous Preterm Birth, International Journal of Molecular Sciences, 2020, 21, 1043, 20 pages.

METHOD AND SYSTEM FOR RAPID PREDICTION OFFAST BLOOD GLUCOSE LEVEL IN PREGNANT SUBJECTS

CROSS REFERENCE OF THE RELATED APPLICATION

The present application claims the benefit of Chinese Patent Application No. 202210083776.9, filed on 24 Jan. 2022, and, 202210083970.7, filed on 24 Jan. 2022. The content of these applications including all tables, diagrams and claims is incorporated hereby as reference it its entirety.

FIELD OF THE INVENTION

The present invention relates to the field of medical diagnosis, specifically relates to a system for screening validated biomarkers for predicting subjects at risk of developing or suffering from gestational diabetes mellitus (GDM).

BACKGROUND OF THE INVENTION

Metabolomics is defined as the comprehensive systematic scientific study of the chemical processes involving metabolites, substrates, intermediates and products of cell metabolism present within an organism, cell, or tissue. The analysis of metabolites can be untargeted (global) or targeted, typically using mass spectrometry-based techniques. Metabolomics of a biological specimen, is an emerging technique that can be applied as a tool for discovering biomarkers. A range of biological functions including energy production, energy storage, and signal transduction are fulfilled in cells through biochemical reactions. These biochemical reactions form part of cell metabolism which generates and utilizes metabolites to fulfill the wide range of functions. Metabolites can be the substrates and products of metabolism. Metabolites can be useful to understand the biochemical reactions their physiological roles. This can be accomplished by identifying metabolites and metabolic pathways that are associated with particular phenotypes.

Gestational diabetes mellitus (GDM) is a condition in which hormones (e.g., estrogen, progesterone, cortisol and human placental lactogen) in the placenta prevent the body from using insulin effectively. As a result, glucose builds up in the blood instead of being absorbed by the cells. Unlike type 1 diabetes, GDM is not caused by a lack of insulin, but rather by other hormones produced during pregnancy that can make insulin less effective, a condition referred to as insulin resistance. There is a risk of increased birth complications with increased fetal birth weight with GDM. GDM is the most common metabolic abnormality during pregnancy, which significantly increases the risk of preterm birth, fetal growth restriction, fetal malformation, and type 2 diabetes in the postpartum mother, etc. In terms of the prevention and control of birth defects, maternal GDM, as a direct "adverse environmental factor", may hinder the normal development of the fetus and lead to embryo-derived adult diseases. GDM symptoms disappear following delivery. Approximately 3 to 8 percent of all pregnant women in the United States are diagnosed with GDM. Any mother can develop gestational diabetes during pregnancy, however there is an increased risk for those who are overweight, have a family history of diabetes, are older than 25, have prediabetes or have a specific racial genetic profile (e.g., African American, American Indian, Asian American, Latino, or Pacific Islander). Therefore, early diagnosis of GDM is very important, as a basis for timely clinical intervention to prevent birth defects and adverse maternal-fetal outcomes. The gold standard of clinical diagnosis is called the oral glucose tolerance test (OGTT). of GDM is based on oral administration of 75 g of glucose solution at 24-28 weeks of gestation, However, the 24-28 week time period for OGTTdiagnosis is often too late to prevent birth defects and adverse maternal-fetal outcomes. Further, patient compliance with instructions is not good, and the adverse effects of hyperglycemia and related metabolic disorders on the mother and child have occurred, which is not conducive to improving the maternal-fetal outcome.

SUMMARY OF THE INVENTION

In an embodiment of the present invention, metabolomics can be used to discover the metabolic markers related to identifying a subject at risk for developing or suffering from a disease, thereby assisting diagnosis and treatment. In an embodiment of the present invention, a criterion for the prediction of GDM can be determined using metabolites in serum collected from normal pregnant women and comparing the metabolite levels with pregnant women with GDM. In an embodiment of the present invention, the quantitation of the metabolite levels can be accomplished using liquid chromatography-high resolution mass spectrometry (LC-HRMS). In an embodiment of the present invention, statistical analysis and modeling can be used to screen for new metabolites to predict whether a pregnant individual is at risk for developing or suffering from GDM. The diagnosis relies upon identifying and distinguishing the differences between the metabolite levels in normal individuals and those with GDM. In an embodiment of the present invention, the metabolite levels for fasting blood glucose levels of pregnant women at 1 hour and 2 hours can be used to predict whether a pregnant individual is at risk for GDM.

An embodiment of the present invention, aims to identify and thereby predict a subject at risk for developing or suffering from a GDM. An embodiment of the present invention, aims to develop a method for identifying new biomarkers of GDM. An alternative embodiment of the present invention, aims to develop a method for identifying new models based on the new biomarkers of GDM. In an embodiment of the present invention, the new biomarkers can be used for identifying and and thereby rapidly predicting a subject at risk for developing or suffering from GDM. In an alternative embodiment of the present invention, the new models and new biomarkers can be used for rapidly identifying and thereby predicting a subject at risk for developing or suffering from GDM. In another embodiment of the present invention, the new models and new biomarkers can be used for rapidly identifying and thereby predicting a subject at risk for developing or suffering from GDM at an early stage.

In a first aspect, the present invention provides a method for screening biomarkers of GDM based on serum metabolomics. The method comprises the followings: specific steps:
  (1) collecting serum samples of pregnant women with GDM diagnosed by OGTT and normal pregnant women confirmed by by OGTTanalysis;
  (2) extracting serum following preparation protocol;
  (3) detecting the extracted serum metabolites and preprocessing data by using liquid chromatography-mass spectrometry;

(4) grouping the samples by utilizing partial least squares discriminant analysis, and screening different metabolites in different groups by combining significance analysis; and (5) mining the biomarkers for diagnosing GDM and application of the biomarkers according to the screened different metabolites, for example, how to diagnose or predict patients with GDM by utilizing the biomarkers, or identify and diagnose the patients with GDM from healthy people.

In some embodiments, the step (1) is specifically implemented as follows: the serum samples are from normal pregnant women and pregnant women with GDM. The normal pregnant women and the pregnant women with GDM are diagnosed and confirmed, such as the normal pregnant women and the pregnant women with GDM confirmed by blood glucose detection and glucose tolerance test.

In some embodiments, the step (2) is specifically implemented as follows: methanol precipitants containing multiple isotope internal standards are added into the serum samples according to a ratio of 1:4, and oscillated for 3 min for uniformly mixing, and then the mixture is centrifuged at 4000×g at 20° C. for 10 min. Four parts of supernatant of which each is 100 μL are taken from each sample and put into four sample plates, the supernatants are blown to be dry by nitrogen, and reconstitution solution containing the isotope internal standards is added for subsequent UPLC-MS/MS detection.

The step (3) is specifically implemented as follows: m/z ions and retention time are extracted from original mass spectrum data, the retention time is collected, then database retrieval is performed to identify metabolites, the chromatographic peak integral of the metabolites is checked to obtain peak area, data normalization and missing value imputation are performed, and subsequent bioinformatic analysis is performed on an obtained data matrix.

The step (4) is specifically implemented as follows: after filtering of the data set, OPLS-DA was applied to the rest of the data set. The result apparently separated the groups into the normal pregnant and those with GDM.

In some embodiments, the step (5) is specifically implemented as follows: compounds with FDR values less than 0.05 and VIP values greater than 1 are screened as significantly differential metabolites or biomarkers in combination with biological significance, biomarkers of the pregnant women with GDM are identified, and metabolic pathway analysis is performed.

Further, after the biomarkers of GDM are screened out, one or more biomarkers are selected to establish a model for differential diagnosis of GDM.

Further, a nonlinear model for predicting the blood glucose level of the pregnant individuals at 1 h or 2 h after 0 h under fasting state is established, the model is optimized, the predicted value of the model is compared with the measured value (OGTT) to verify the accuracy of model diagnosis, and finally a better diagnosis model is obtained.

Therefore, in a second aspect, the present invention provides application of biomarkers in a detection reagent for diagnosing whether a pregnant individual suffers from diabetes, and the biomarkers are selected from one or more of the following: (R)-3-hydroxybutyrylcarnitine, 1,5-anhydroglucitol (1,5-AG), 1-arachidonoyl-GPC (20:4), 1-arachidonoyl-GPI (20:4), 1-linoleoyl-GPC (18:2), 1-palmitoyl-GPA (16:0), 1-palmitoyl-GPC (16:0), 2-aminoadipic acid, 2-hydroxybutyrate (AHB), 3-(4-hydroxyphenyl)lactate (HPLA), 3-hydroxybutyrate (BHBA), 3-methyl-2-oxobutyrate, 3-methyl-2-oxovalerate, 4-methyl-2-oxopentanoate, 8-methoxykynurenate, carnitine, cis-3,4-methyleneheptanoylcarnitine, cystathionine, cysteinylglycine disulfide, deoxycholate, γ-glutamyl-epsilon-lysine, glucose, glycerophosphoinositol, glycine, glycocholenate sulfate, glycolithocholate sulfate, histidylalanine, indolelactate, isoleucine, isoursodeoxycholate sulfate (2), isovalerate (C5), lanthionine, leucine, N6-acetyllysine, N-acetyltaurine, N-acetyltryptophan, N-acetylvaline, oleate, orotidine, oxalate (ethanedioate), palmitoylcarnitine, pantothenic acid, phenylalanine, pyroglutamine, serine, threonate, tyrosine, valine.

Preferably, the GDM, particularly the early-to-mid GDM, is within 28 weeks of pregnancy, such as within 1-20 weeks of pregnancy, such as within 1, 2, 3, 4, 5, 6, 7, 8, 9, 10, 12 or 14 weeks of pregnancy.

In some embodiments, the biomarkers are selected from one or more of the following: (R)-3-hydroxybutyrylcarnitine, 1-arachidonoyl-GPC (20:4), 1-arachidonoyl-GPI (20:4), 1-linoleoyl-GPC (18:2), 1-palmitoyl-GPA (16:0), 1-palmitoyl-GPC (16:0), 3-(4-hydroxyphenyl)lactate (HPLA), 3-methyl-2-oxobutyrate, 8-methoxykynurenate, cis-3,4-methyleneheptanoylcarnitine, cysteinylglycine disulfide, γ-glutamyl-epsilon-lysine, glycerophosphoinositol, histidylalanine, indolelactate, isoursodeoxycholate sulfate (2), N6-acetyllysine, N-acetyltaurine, N-acetyltryptophan, N-acetylvaline, orotidine, oxalate (ethanedioate), pantothenic acid.

In some embodiments, the biomarkers are selected from one or more of the following: 1-arachidonoyl-GPI (20:4), 1-palmitoyl-GPA (16:0), 8-methoxykynurenate, cis-3,4-methyleneheptanoylcarnitine, cysteinylglycine disulfide, γ-glutamyl-epsilon-lysine, glycerophosphoinositol, histidylalanine, isoursodeoxycholate sulfate (2), N6-acetyllysine, N-acetyltaurine, N-acetyltryptophan, N-acetylvaline, orotidine, oxalate (ethanedioate).

In some embodiments, the biomarkers are selected from one or more of the following: 8-methoxykynurenate, cysteinylglycine disulfide, histidylalanine, isoursodeoxycholate sulfate (2).

In a third aspect of the present invention, a classification model is established for jointly identifying and diagnosing whether the pregnant individuals suffer from diabetes or not by using a plurality of biomarkers. The classification model can be used for distinguishing GDM from non-GDM, distinguishing a plurality of pregnant women in a gestational period into a GDM group and a non-GDM group, and finding out GDM pregnant women in the plurality of pregnant women in the gestational period. For example, when there are about 20 GDM patients in 300 pregnant women, and the GDM patients in the 300 pregnant women need to be found out or the 300 pregnant women are divided into the GDM group and the non-GDM group, the classification model can be used for identifying them.

In some embodiments, the classification model is one of model A, model B, model C, model D and model E, and the equations of the classification model are as follows:

Score=3.425*glucose+0.854*palmitoylcarnitine−4.598*oleate−1.307*glycine+0.309*phenylalanine−2.253*Serine−0.335*tyrosine−0.172*isoleucine−1.273*leucine−0.422*valine+0.622*2-aminoadipic acid−0.882*1,5-anhydroglucitol (1,5-AG)+0.898*3-methyl-2-oxobutyrate+2.292*3-hydroxybutyrate (BHBA)+2.919*2-hydroxybutyrate (AHB)+1.319*pantothenic acid−0.103*3-methyl-2-oxovalerate+0.856*4-methyl-2-oxopentanoate+1.256*1-palmitoyl-GPC (16:0).     Model A:

Score=−0.0199*deoxycholate−0.290*N-acetylvaline−
 0.400*carnitine+0.161*cystathionine−0.244*in-
 dolelactate+0.177*oxalate (ethanedioate)+
 0.127*threonate+0.00588*3-(4-hydroxyphenyl)
 lactate (HPLA)−0.0284*glycocholenate sulfate+
 0.0678*glycolithocholate sulfate+0.484*1-
 arachidonoyl-GPC (20:4)−0.431*gamma-
 glutamyl-epsilon-lysine+0.177*N-
 acetyltryptophan+0.0495*1-arachidonoyl-GPI
 (20:4)−0.214*1-linoleoyl-GPC (18:2)−0.0635*1-
 palmitoyl-GPA (16:0)−0.0171*orotidine+
 0.415*N6-acetyllysine+0.0039*lanthionine−
 0.0893*histidylalanine−0.0995*(R)-3-
 hydroxybutyrylcarnitine−0.0756*isovalerate
 (C5)+0.146*pyroglutamine+0.0503*glycero-
 phosphoinositol+0.0513*N-acetyltaurine−
 0.0205*cysteinylglycine disulfide+0.187*8-
 methoxykynurenate−
 0.0361*isoursodeoxycholate sulfate (2)+
 0.142*cis-3,4-methyleneheptanoylcarnitine.                Model B:

Score=1-palmitoyl-GPC (16:0)*0.163+palmitoylcar-
 nitine*1.775+oleate*0.455 glycine*0.723+phe-
 nylalanine*0.203+Serine*0.085−tyrosine*1.599−
 isoleucine*0.271−leucine*1.177+valine*0.506+
 2-aminoadipic acid*1.622.                                Model C:

Score=1.847*palmitoylcarnitine+0.447*oleate−
 0.757*glycine+0.235*phenylalanine+0.057*Ser-
 ine−1.606*tyrosine−0.285*isoleucine−
 1.103*leucine+0.491*valine+1.622*2-
 aminoadipic acid.                                        Model D:

Score=0.688*oleate−0.78*glycine+0.484*phenylala-
 nine+0.146*Serine−0.781*tyrosine+0.383*iso-
 leucine−1.431*leucine+0.303*valine+1.27*2-
 aminoadipic acid.                                        Model E:

In some of embodiments, the name of each biomarker represents the relative abundance of the corresponding biomarker in serum sample of pregnant women.

In some embodiments, the critical value of a model A is 0.515, and the relative abundance of the corresponding compound in the serum is input into the model A; when Score is >0.515, the probability of diagnosing as GDM is high, and when Score is ≤0.515, the probability of diagnosing as GDM is low or the pregnant individual is directly judged as normal pregnancy.

The critical value of a model B is 0.463, and the relative abundance of the corresponding compound in the serum is input into the model B: when Score is >0.463, the probability of diagnosing as GDM is high or the pregnant individual is diagnosed as GDM directly, and when Score is 0.463, the probability of diagnosing as GDM is low or the pregnant individual is directly judged as normal pregnancy.

The critical value of the model C is 0.662, and the relative abundance of the corresponding compound in the serum is input into the model C: when Score is >0.662, the probability of diagnosing as GDM is high, and when Score is ≤0.662, the probability of diagnosing as GDM is low.

The critical value of the model D is 0.661, and the relative abundance of the corresponding compound in the serum is input into the model D: when Score is >0.661, the probability of diagnosing as GDM is high, and when Score is ≤0.661, the probability of diagnosing as GDM is low.

The critical value of the model E is 0.671, and the relative abundance of the corresponding compound in the serum is input into the model E: when Score is >0.671, the probability of diagnosing as GDM is high, and when Score is ≤0.671, the probability of diagnosing as GDM is low.

The above models are used for verifying that the distinguishing accuracy of diabetes in the actual pregnant woman group and the correlation of actual data are 0.950, and it is indicated that the normal pregnant woman and the pregnant woman with diabetes can be distinguished through these models.

In some embodiments, the steps of detecting the relative abundance of corresponding marker compounds in serum include:
  step 1: collecting serum samples to be detected;
  step 2: extracting serum metabolites; and
  step 3: performing detecting and data processing on the serum metabolites in the step 2 through liquid chromatography-mass spectrometry.

In some embodiments, the specific operation of extracting the serum metabolites in the step 2 comprises the steps: methanol precipitators are added into the serum samples according to the proportion of 1:4 and oscillated for 3 min for uniformly mixing, and then the mixture is centrifuged at 4000×g at 20° C. for 10 min. Four parts of supernatant of which each is 100 µL are taken from each sample and put into four sample plates, the supernatants are blown to be dry by nitrogen, and a reconstitution solution is added for subsequent detection.

In some embodiments, the reconstitution solution contains multiple isotope internal standards.

In some embodiments, the detection conditions of liquid chromatography-mass spectrometry comprise:
  detecting by adopting UPLC-Q Exactive, wherein the scanning range is 70-1000 m/z; when detecting by adopting a positive ion electrospray ionization mode, separating by using a C18 chromatographic column, wherein a mobile phase A is water containing 0.05% of PFPA and 0.1% of FA, and a mobile phase B is methanol or a mixed solution of methanol, acetonitrile and water; and
  when detecting by adopting a negative ion electrospray ionization mode, separating by using the C18 chromatographic column, wherein the mobile phase A is water containing 6.5 mM of ammonium bicarbonate, and the mobile phase B is methanol (B); or separating by using an HILIC chromatographic column, wherein the mobile phase A is water containing 10 mM of ammonium formate, and the mobile phase B is acetonitrile.

It should be noted that, the relative abundance mentioned herein is the relative value or level of the amount of each biomarker. For example, the total amount of all biomarkers of model A in a certain sample is X, and the amount of glucose is A, then the relative abundance of glucose is the ratio of A to X. The amount herein can be expressed as concentration, content or weight; or can be expressed as the intensity of ultraviolet absorption, the intensity of fluorescence, the area of chromatographic peaks or the height of peaks, etc. In some embodiments, the amount of an internal standard or a compound can be used as a reference, and the relative abundance of a biomarker is the ratio of the amount of the biomarker to the amount of the internal standard or the compound. At this time, the critical value of the model needs to be changed accordingly or the model coefficients of each biomarker in the model need to change proportionally. In some embodiments, the relative abundance herein can be the absolute value of the amount of each biomarker, for example, the concentration or content in the sample to be tested, at this time, the critical value of the model needs to be changed accordingly or the model coefficients of each biomarker in the model need to change proportionally.

In some embodiments, ROC curves are established for each biomarker, and those biomarkers with large areas under the curve (AUC) can be found, so that a batch of biomarkers can be selected to establish a diagnostic model as to achieve a more reliable diagnostic result. It is generally understood that the more biomarkers selected, the higher the reliability of the established model may be, for example, the higher the accuracy and specificity, the higher the sensitivity. However, it is also possible to select a single or several important biomarkers for diagnosis, or to perform preliminary screening and testing. The test method can be any existed methods, for example, by using the LC-MS of the present invention, one or more biomarkers can be detected at one time in a high-throughput manner. Of course, the detection of a few numbers of several biomarkers is not excluded. Certainly, immunological methods can also be used to detect a few numbers of important biomarkers, for example, the combined detection of 1, 2, 3, 4 or 5 biomarkers has diagnostic value, for example, the amount of a single marker glucose in the blood is used to measure whether an individual has diabetes, which is also a gold standard, but it does not mean that glucose is the sole marker. Of course, other markers can be selected to measure, for example, newly discovered markers in the present invention can be used to determine whether an individual has suffered from GDM.

In a fourth aspect, the present invention provides a prediction model for predicting the blood glucose level. The prediction model can be a linear model or a nonlinear model, such as one of a random forest regression tree, a polynomial regression tree, a support vector regression tree and a gradient boosting regression tree, and preferably, a support vector regression model.

The prediction model can be established by selecting one or more GDM biomarkers, for example, a combination of one or more of the above biomarkers, and of course other reported GDM biomarkers or a combination thereof. The blood glucose level of a pregnant individual can be predicted through the prediction model, for example, the blood glucose level can be predicted by inputting the detection value or the test concentration value of the biomarker into the prediction model. In some embodiments, markers for predicting pregnant individuals can be selected and used in combination, or the concentration values of markers in fasting blood samples can be used and input into the model of the present invention, to predict the blood glucose levels at 1 hour and 2 hours after 0 h under the fasting sate.

In some embodiments, the prediction model is the support vector regression model, and the equation of the support vector regression model is:

$$Y = \sum_{i=1}^{m} W_i \cdot K_i + b$$

where Y is the predicted blood glucose level, i represents the ith biomarker, m represents the number of biomarkers, $W_i$ represents the weighted value of the ith biomarker, $K_i$ represents the coefficient of the ith biomarker, and b is a constant.

In some embodiments, $K_i$ is calculated by the following formula:

$$K_i = (\gamma \cdot \mu_i \cdot v_i + \text{coef})^{degree}$$

where $\gamma$, coef and degree are parameters to be adjusted, $\mu_i \cdot v_i$ is a linear model of independent variables, i is the linear coefficient of the ith biomarker, and vi is the detection value or the test value of the ith biomarker. The test value could be a concentration of ith biomarker in blood sample taken from a pregnant woman.

In some embodiments, when 19 biomarkers are selected to establish a support vector regression model, m is 19.

Preferably, the 19 biomarkers consist of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleate, glycine, phenylalanine, serine, tyrosine, isoleucine, leucine, valine and 2-aminoadipic acid.

W1, W2 ... W19 are respectively the weights of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleate, glycine, phenylalanine, serine, tyrosine, isoleucine, leucine, valine and 2-aminoadipic acid.

μ1, μ2 ... μ19 are respectively linear coefficients of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleate, glycine, phenylalanine, serine, tyrosine, isoleucine, leucine, valine and 2-aminoadipic acid. v1, v2 ... v19 are respectively detection values of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleate, glycine, phenylalanine, serine, tyrosine, isoleucine, leucine, valine and 2-aminoadipic acid in the serum of the individual.

In some embodiments, when the blood glucose level at a certain time point 0 h under fasting state is predicted by detecting serum of 0 h under fasting state, the detection value is the serum concentration of a biomarker of the individual 0 h under fasting state.

In some embodiments, when the support vector regression model is used to predict the blood glucose level at 1 h after fasting state, b=0.0628, γ=0.037, coef=1, degree=3, W1, W2 . . . W19 are respectively: −140.1367461, −18.20203701, −0.266373135, −3.780820943, 0.703137151, 0.012695848, 0.390205074, −0.34291643, −8.627272594, 0.012476258, 4.889600901, 0.140125414, −2.270950842, −3.66914922, 1.697783174, −1.961842966, −6.56784338, −4.497375666, −0.037450268, μ1, μ2 ... μ19 values are respectively: −5.94596E-05, −0.026149544, 0.28517657, 0.0073573, 0.265723742, 11.02574829, 0.671723153, −0.753129322, −0.000533758, 28.73541414, 0.009542539, 0.023184566, 0.066366599, −0.022813626, −0.151902626, 0.053198092, 0.051457031, 0.005974243, 2.289641593.

In some embodiments, when the support vector regression model is used to predict the blood glucose level at 2 h after 0 h under fasting state, b=0.0797, γ=0.037, coef=2, degree=3; W1, W2 ... W19 are respectively: −98.73331703, 3.187643085, −0.21586202, −12.36378322, −2.548963953, −0.290267916, 0.192553693, −0.858808125, 15.2824188, −0.009794368, −17.62280907, −6.38707688, −5.655502071, −2.357173357, −0.809820523, 1.810651075, 0.243270797, −3.100345313, −0.150868078, μ1, μ2 ... μ19 values are as follows: −0.000356085, −0.033072209, 0.35070682, −0.003628292, 0.227143481, 10.14047839, 0.684864863, −0.675811046, 0.011682708, 3.438905244, 0.011565459, 0.050289956, −0.022181694, −0.038488107, −0.175825644, 0.165291135, 0.077198939, −0.070012174, 1.889998371.

It should be noted that, in some embodiments, the detection value is obtained, and substituted into the support vector regression model system. The model can be used to predict the blood glucose concentration at 1 hour and 2 hours after 0 h under fasting state, and can also be used to predict the results of oral glucose tolerance test (OGTT). By comparing the prediction result of the model with the traditional standard value of blood glucose, it can be judged whether a pregnant individual suffers from GDM. In some embodiments, the detection value herein can be a serum level, relative abundance in a serum, or the concentration or level or relative abundance of biomarkers in other body fluids, such as a urine liquid, in addition to the serum concentration of the above biomarkers. The method for obtaining the detection value may be LC-MS or other analytical methods capable of detecting the concentration of the biomarkers, such as gas chromatography, UV, infrared, NMR chromatography or immunoassay, etc. Such a formula or a model is used to predict, for example, by taking samples under a fasting state, measuring the concentration or content of the selected markers, then the predicted blood glucose level can be calculated using the above selected markers, such as the weighted value of each marker (calculated in advance), the concentration value (sample measurement) and coefficient value (calculated by modeling in advance), and the prediction formula of the present invention. Unlike the conventional method of oral glucose tolerance test (OGTT), this method of this invention can avoid the drawback of conventional method. Such that, in the present invention, there is no need to oral glucose take under fasting state and just take a blood sample from pregnant woman who is under the fasting state. And then test the concentration of the selected biomarkers in the blood sample, final input the concentration of each biomarker into the model of present invention to predicted the blood glucose level in 1 or 2 hours after fasting state. Furthermore, early prediction can be performed, for example, at 1 week, 2 weeks, 3 weeks, 4 weeks, 5 weeks, 8 weeks, 12 weeks, or 18 weeks, or 20 weeks of gestation. Finally, samples are taken only one time for this method, while samples are taken at least twice for testing for the conventional OGTT method.

In some embodiments, a system containing the above models is provided, the system comprises the above models or model formulas, then measured values of biomarkers are input, and then the system automatically calculates the predicted blood glucose level, or a computer automatically calculates whether an individual is GDM or not. Therefore, the system comprises an input module and a calculation or operation module, the input module is used for inputting the measured values of the biomarkers, such as concentration values. A storage module included in this system is used for storing the concentration values of the biomarkers, then the calculation system automatically extracts the concentration values from the storage module and brings the concentration values into the model formulas for operation. Coefficient values and weighted values of the markers can also be stored in the storage in advance, and during calculation, the coefficient values and the weight values are automatically extracted and brought into the model formulas for calculation to obtain results, such as the blood glucose level or the normal or diabetic pregnant individuals.

In some embodiments, the present invention provides a method for establishing a support vector regression model. The method comprises the following steps:

step (1): acquiring sample data, such as the concentration of multiple biomarkers of a patient 0 h under fasting state and the blood glucose level of the patient 1 h and 2 h after fasting state;

step (2): randomly dividing the sample data obtained in the step (1) into a training set and a validation set;

step (3): performing high-dimensional mapping by adopting a polynomial kernel function K (X), wherein the mathematical expression of the polynomial kernel function is:

$$K(X)=(\gamma \cdot X+\text{coef})^{degree}$$

$$X=\mu_i \cdot v_i$$

where $\gamma$, coef and degree are parameters to be adjusted, $\mu_i \cdot v_i$ is a linear model of the independent variable, $\mu_i$ is a linear coefficient of the $i^{th}$ biomarker, and $v_i$ is a data value of the $i^{th}$ biomarker obtained in the step (1); and step (4): training the model through the training set data, wherein parameter adjustment adopts a mode of combining grid search and gradient descent, the most possible range of the optimal parameter is defined, all parameter combinations are traversed in the defined range, the support vector regression model containing a certain number of support vectors is obtained, and the accuracy of the model is verified by using the validation set. The support vectors form a "spacer belt" in a high-dimensional space, and the distance between the sample vector and the edge of the "spacer belt" is calculated through a formula when a new sample is predicted, so that the predicted final value, namely the predicted blood glucose level, is obtained.

In some embodiments, the training set accounts for 80% of the total number of sample data, and the validation set accounts for 20% of the total number of samples. In addition, sample data may also be divided into a training set and a validation set in a ratio of 1:1 or otherwise, generally the training set having no less sample data than the validation set.

In a fifth aspect of the present invention, the present invention provides an early diagnosis system for GDM. The diagnosis system comprises an operation module.

In some embodiments, the operation module comprises one or more of classification models for jointly identifying and diagnosing whether the pregnant individuals suffers from diabetes or not by using various biomarkers in the third aspect. The relative abundance of the biomarkers of the pregnant individuals is input into the system, and the system can distinguish whether the pregnant woman suffers from GDM or non-GDM; or the relative abundance of the biomarkers of a plurality of pregnant women (including pregnant women with GDM and normal pregnant women) is input into the system, and the system can divide the plurality of pregnant women into a GDM group and a non-GDM group.

In some embodiments, the operation module comprises a prediction model for predicting the blood glucose level in the third aspect. The detection value of the biomarker of the pregnant individuals measured 0 h under fasting state is input into the system, and the system can predict the blood glucose level at a certain time (such as 1 h and/or 2 h) after 0 h under fasting state. Preferably, the system can also compare the predicted blood glucose level with a standard value, and therefore as to judge or determine whether the pregnant individuals suffers from diabetes or the possibility of suffering from diabetes.

In some embodiments, the diagnosis system further comprises an input module, the input module is used for inputting one or more detection results of the biomarkers, and the detection results can be quantitative detection results or qualitative results, like a concentration of one or more than one biomarkers in a liquid sample, such as a blood sample.

In some embodiments, the diagnostic system comprises a detection module, wherein the detection module is used for detecting the samples, and the quantity, such as concentration and relative abundance, of each biomarker. The system comprises a measurement module, wherein the measurement module is used for detecting specific markers in a sample, and the detection module can be a liquid phase-mass spectrometer, a fluorescence instrument for detecting antigen-antibody reaction, etc. The specific diagnosis or detection method can be the existing conventional methods, such as liquid chromatography, gas chromatography, capillary electrophoresis, supercritical fluid chromatography, ion chromatography and other chromatographic methods, mass spectrometry and the combination technology of the mass spectrometry and the chromatography, nuclear magnetic, ultraviolet, infrared and other spectroscopy, immune methods, etc. The immune methods comprise enzyme-linked immunosorbent assay, dry chemical method, dry test strip method or electrochemical method.

In some embodiments, the diagnostic system comprises a judgment module, and the judgment module judges the relation between a calculation result of an operation module and a critical value to obtain a final diagnostic result.

In some embodiments, the diagnostic system further comprises an output module used for outputting the diagnostic result.

In some embodiments, the diagnostic system further comprises a negative control or reference data module.

In a seventh aspect of the present invention, the present invention provides a kit for detecting GDM mellitus or biomarkers. The kit comprises one or more reagents capable of detecting biomarkers, wherein the reagents can be blood sample treatment reagents, such as reagents for filtering and extracting the biomarkers from the blood sample, and also comprise reagents directly used for detecting whether the biomarker exists or not or a concentration of the biomarker, and the reagents could be antibodies, antigens or markers.

The system has the advantages that small molecule difference of metabolites between a pregnant woman with GDM mellitus and a normal pregnant woman are screened out by using a serum metabolomics method. These new biomarkers are used to identify GDM. In addition, the present invention also provides a model for accurately differential diagnosing GDM mellitus.

DETAILED DESCRIPTION (1) Diagnosis or Detection

Figure 1:
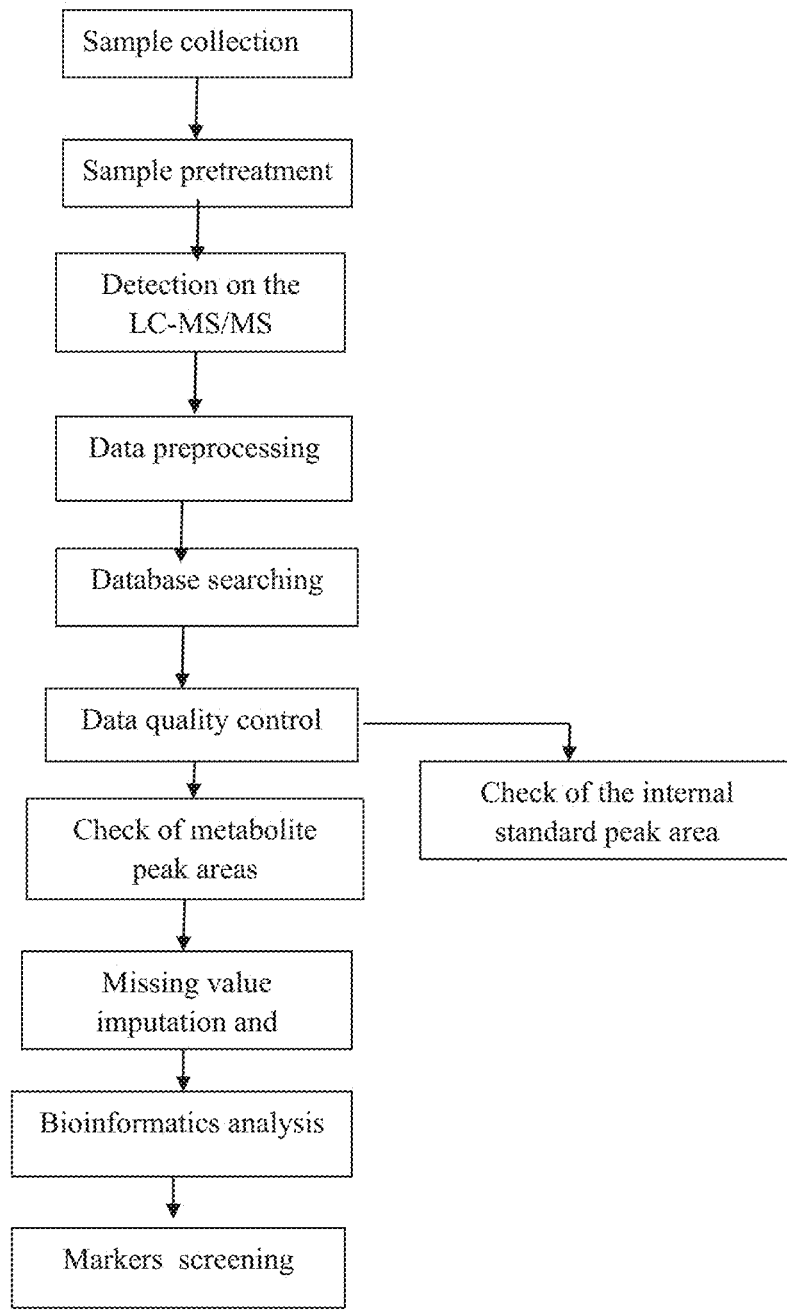
FIG. 1 is a flow chart for analysis.
Figure 2:
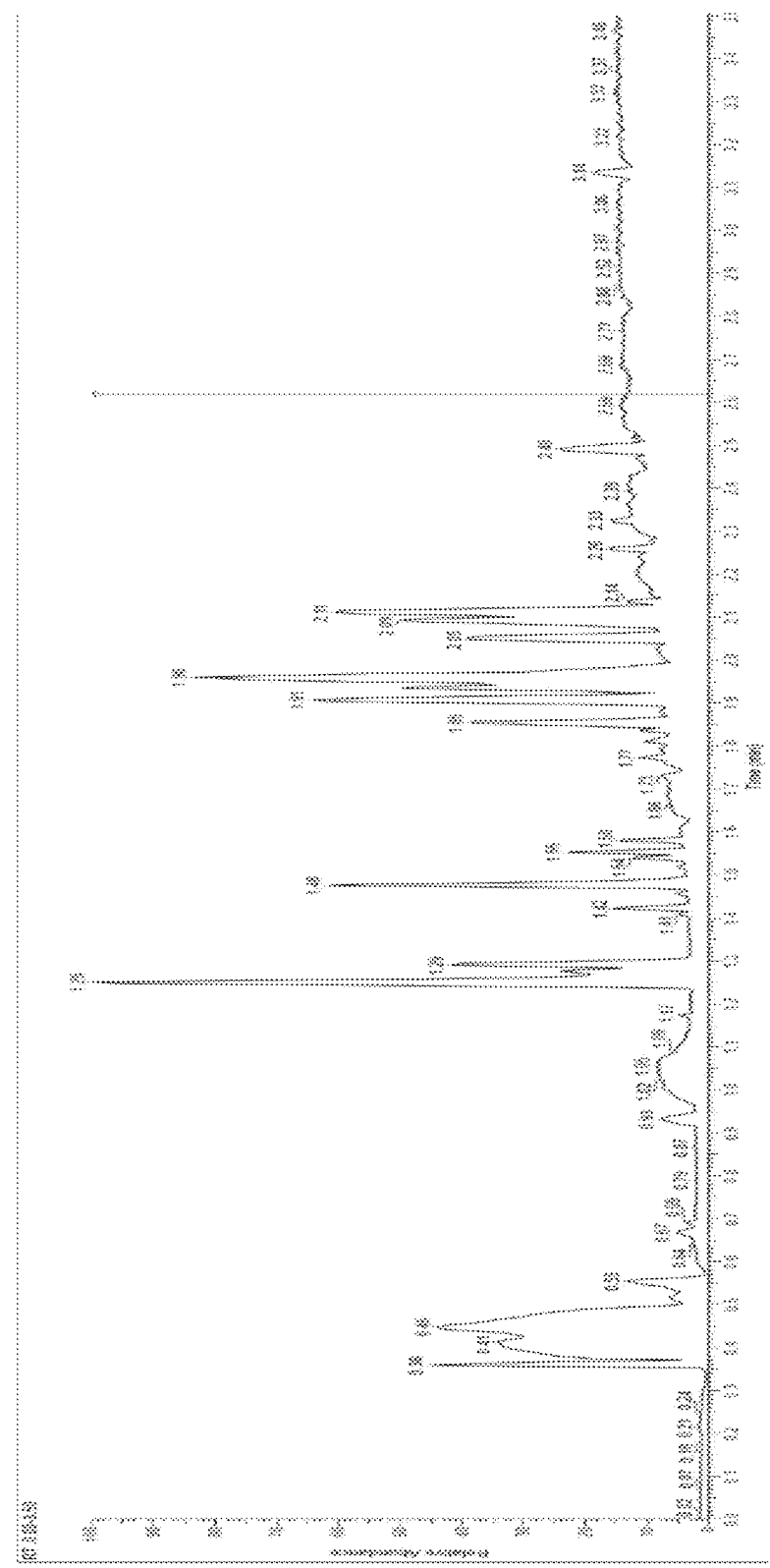
FIG. 2 is a total ion chromatogram in positive ion mode.
Figure 3:
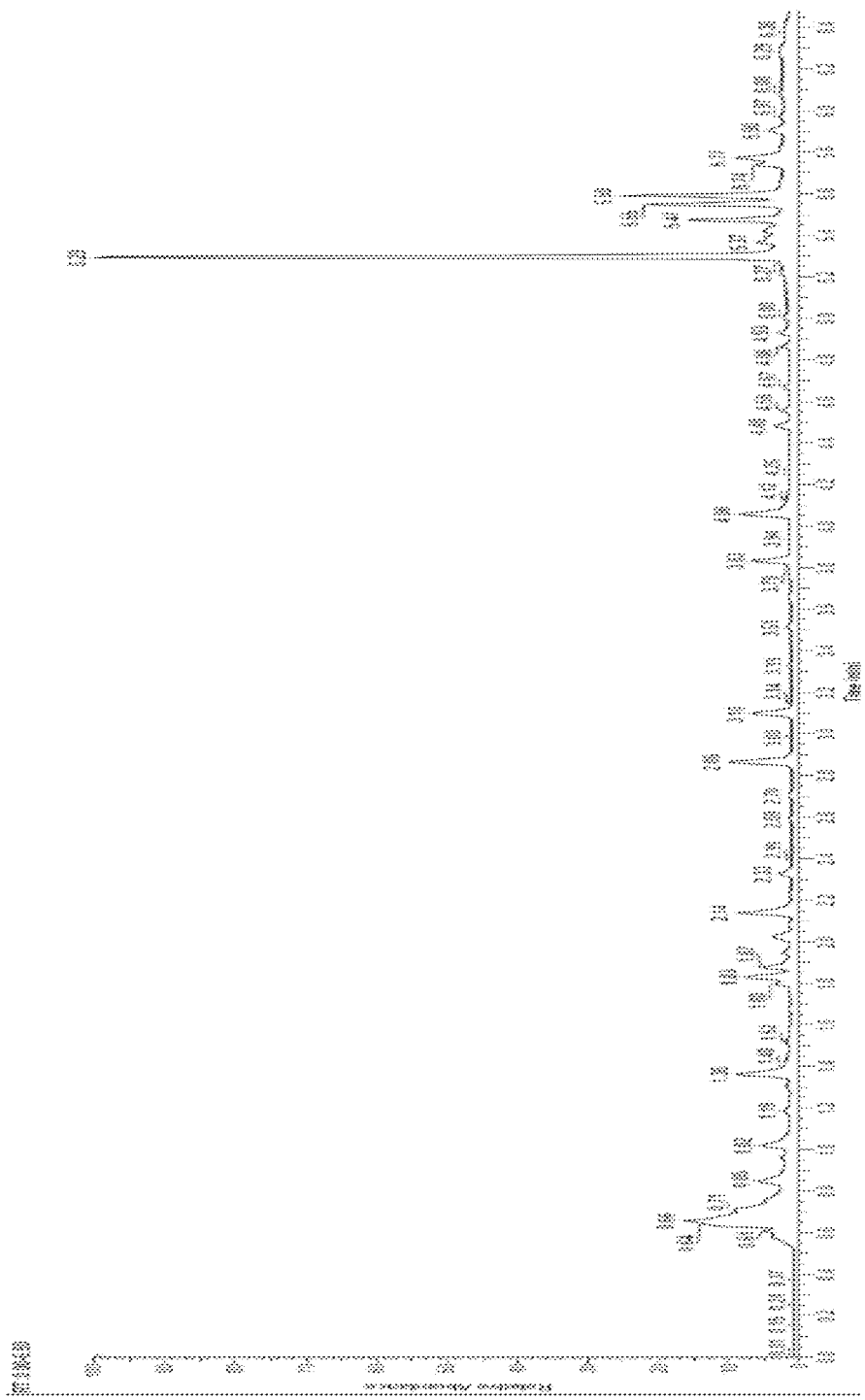
FIG. 3 is a total ion chromatogram in negative ion mode.

The diagnosis or detection herein refers to the detection or assay of the biomarkers in the sample, or the content of target biomarkers, for example, the absolute content or relative content, and then the presence or quantity of the target markers is used to illustrate whether an individual is likely to have or suffer from a disease, or the likelihood of having a disease. The meanings of diagnosis and detection are interchangeable herein. The detection or diagnosis results cannot be directly used as a direct result, but an intermediate result of a disease. If a direct result is obtained, other auxiliary means such as pathology or anatomy can be used to confirm that an individual has a certain disease. For example, the present invention provides a variety of new biomarkers that are associated with GDM, and changes in the levels of these markers are directly correlated with GDM.

(2) Relevance Between Markers or Biomarkers and GDM

Markers and biomarkers have the same meaning in the present invention. The relevance means that the appearance or content change of a certain biomarker in a liquid sample has a direct relevance with a specific disease, for example, a relative increase or decrease in the level of biomarkers indicates that the possibility of having this disease is relatively higher than healthy individuals.

If multiple different markers appear at the same time or there is relative change in their levels in the samples, it indicates that the possibility of having this disease is relatively higher than healthy individuals. Among these markers, some markers are strongly correlated with disease, some markers are weakly correlated with disease, or some are not even correlated with a specific disease. One or more of those markers with strong correlation can be used as markers for diagnosing diseases, and those markers with weak correlation can be combined with strong markers to diagnose a certain disease, increasing the accuracy of test results.

For a plurality of biomarkers in serum found in the present invention, these markers can be used to distinguish GDM patients from healthy pregnant women. The marker can be used as a single marker for direct detection or diagnosis. such a marker that is selected indicates that the relative change in the level of the marker has a strong correlation with GDM. Of course, it can be understood that the simultaneous detection of one or more markers strongly associated with GDM can be performed. Generally, in some embodiments, detection or diagnosis by using the biomarkers with strong correlation can achieve a certain standard of accuracy, for example, accuracy of 0%, 65%, 70%, 80%, 85%, 90% or 95%. it can be understood that these markers can obtain the median value for diagnosing a certain disease, but it does not mean that an individual can be confirmed to have a certain disease. For example, in the present invention, for the differential metabolites shown in Table 2, those with higher VIP value or higher FC value can be selected as markers for diagnosing GDM, or as markers for screening GDM from healthy pregnant women.

Of course, differential metabolites with larger ROC values can also be selected as diagnostic markers. The "strong" or "weak" is generally confirmed by some algorithms, for example, the contribution rate or weighted value analysis of markers and GDM. Such calculation methods can be significance analysis (p value or FDR value) and fold change, and multivariate statistical analysis mainly includes principal component analysis (PCA), partial least squares-discriminant analysis (PLS-DA) and orthogonal partial least squares discriminant analysis (OPLS-DA), of course, also it includes other methods, such as ROC analysis. Of course, other model prediction methods are also possible be used. When selecting specific biomarkers, the differential metabolites disclosed in the present invention can be selected, or other existing well-known markers can be selected or combined together.

(3) Diabetes and GDM

Diabetes is a metabolic disease characterized by elevated levels of blood glucose in patients. Diabetes is due to either the pancreas not producing enough insulin, or the cells of the body not responding properly to the insulin produced. The types of diabetes mellitus include type I diabetes, type II diabetes and GDM, etc. Type I diabetes results from failure of the pancreas to produce enough insulin or to produce any insulin, also known as insulin-dependent diabetes. For patients with type II diabetes, their own pancreas have no pathological problems, but the cells do not respond properly to, and are insensitive to or do not respond to insulin. It is also known as non-insulin-dependent diabetes. GDM occurs when pregnant women without a previous history of diabetes develop higher blood sugar levels than normal levels during pregnancy.

According to the above classification, GDM is significantly different from type I diabetes and type II diabetes. GDM occurs in a specific period and in a specific population. There is a series of difference in the in-vivo metabolism between the pregnant women and normal people, and the serum metabolites are also different. Therefore, biomarkers (including serum biomarkers), which are used for the diagnosis of type I diabetes or type II diabetes, can not be used to identifying o GDM, for example, Joanna Hajduk et al. reported that there was no significant difference in alanine level between the control group and GDM group (p>0.1) (A Combined Metabolomic and Proteomic Analysis of GDM Mellitus, International Journal of Molecular Sciences, 2015, 16, 30034-30045). However, Sanmei Chen et al. reported that alanine was closely related to type II diabetes mellitus and was a potential biomarker to type II diabetes (Serum amino acid profiles and risk of type 2 diabetes among Japanese adults in the Hitachi Health Study, Scientific Reports, 2019, 9:7010). Likewise, biomarkers that are applicable to the diagnosis of GDM can not be necessarily applicable to the diagnosis of type I diabetes or type II diabetes.

In addition, obesity is a high-risk factor for diabetes (including GDM), but it is not an absolute factor, and the biomarkers of obesity are not the biomarkers of diabetes or GDM. For example, U.S. Ser. No. 16/375,834 discloses that glutamate is a differential metabolite of obesity. Kalliopi I. Pappa et al. reported that there was no significant difference in glutamate between normal pregnant women group and pregnant women with GDM group (Intermediate metabolism in association with the amino acid profile during the third trimester of normal pregnancy and diet-controlled gestational diabetes, American Journal of Obstetrics & Gynecology, 2007, 1).

DETAILED DESCRIPTION OF THE INVENTION

In order to describe the present invention more specifically, the technical solutions of the present invention will be described in detail below with reference to the accompanying drawings and specific embodiments. These descriptions merely illustrate how the present invention is implemented, and do not limit the protection scope of the present invention. The protection scope of the present invention is defined by the claims.

Definitions

Techniques for formulation and administration of the disclosed compounds of the application can be found in Remington: the Science and Practice of Pharmacy, 19th edition, Mack Publishing Co., Easton, PA (1995) which is herein incorporated by reference for all purposes. In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein. Compounds and compositions of the application can be administered in therapeutically effective amounts in a combinational therapy with one or more therapeutic agents (pharmaceutical combinations) or modalities, e.g., anti-proliferative, anti-cancer, immunomodulatory, or anti-inflammatory agent, and/or non-drug therapies, etc. For example, synergistic effects can occur with anti-proliferative, anti-cancer, immunomodulatory, or anti-inflammatory substances. One skilled in the art will appreciate that it is sometimes necessary to make routine variations to the dosage depending on the age and condition of the patient. A patient's dosage is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight. The term "about" means in the absence of an express range, the nominal value plus or minus a range of ten (10) percent thereof.

A subject means a mammal in which the mammal's health is to be assayed. In an embodiment the mammal is a human. In an alternative embodiment the mammal is porcine, bovine, equine, ovine, murine, and *rattus*. A human subject means a patient in which the patient's health is to be assayed. The dosage administered to a patient will depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required. The pharmaceutical compositions containing active compounds of the present application can be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. The appropriate formulation is dependent upon the route of administration chosen.

A biomarker means an intermediate or end product of the metabolism of a compound imbibed, introduced into or otherwise synthesized by an organism. A biomarker is often a metabolite, that can be differentially present (i.e., increased or decreased) in a subject.

An assay means an investigative medical procedure (which may be carried out in a laboratory) for qualitatively assessing or quantitatively measuring the presence, amount, or functional activity of one or more biomarkers.

The 'detection of the metabolites in the sample' means the determination of the absolute abundance and/or relative abundance of a metabolite. The detection involves a statistical evaluation of the abundance of a metabolite. The detection can involve a comparison to a known level, a previously determined level, or a reference level of the metabolite. In an alternative embodiment of the invention, the reference level of a metabolite can be determined from a reference library. A metabolite selected as a biomarker is therefore also 'detected'.

Prediction means a statement about identifying the level of a chemical in a sample taken from a subject, e.g., a level of glucose in the blood of a patient. A prediction can also be made based on the identification of the chemical in the sample about a subject developing a malady in the future based on the level of the chemical in the sample, provided there is independent evidence to correlate the level of the chemical in the sample with the malady.

Evaluation means a judgment based on detection of metabolites in a sample about a subject developing a malady in the future. An evaluation can be used to identify a subject at risk of developing or suffering from a malady for further diagnostic testing.

Diagnoses or diagnosing is the identification of a disease via medical examination, allowing a prognosis to be developed for predicting the course of the disease as well as the course for a treatment and results. A diagnosis can follow a prediction and/or an evaluation requiring further examination not undertaken as part of the prediction and/or the evaluation.

Body Mass Index (BMI) is germane to a number of diseases including hypertension, kidney disease, gallstones, steato hepatitis, lung disease, type 2 diabetes, heart disease and certain cancers.

The interconnection means that a patient suffers from a disease (e.g., GDM) based on the detection of the biomarkers meeting the criteria as set out herein. An interconnection that a patient suffers from a disease (e.g., GDM) based on the detection of the biomarkers, requires confirmation by other means such as pathology tests and/or anatomical evaluation in order to confirm that the patient suffers from the GDM disease.

A sample means biological material isolated from a patient. The biological sample may contain any biological material suitable for detecting metabolites comprising cellular and/or non-cellular material from the patient. The sample can be isolated from blood samples (e.g., whole blood, plasma, serum), other biological fluids (e.g., saliva, urine, fecal) or biological material (e.g., tissue, skin).

A metabolite means an intermediate or end product of the metabolism of a compound imbibed, introduced into or otherwise synthesized by an organism. A metabolite at least includes bile acid metabolites, glucose; 1,5-anhydroglucitol; 3-methyl-2-oxobutyrate; 3-hydroxybutyrate; 2-hydroxybutyrate; pantothenic acid; 3-methyl-2-oxovalerate; 4-methyl-2-oxovalerate; palmitoyl-GPC; palmitoylcarnitine; oleic acid; amino acids, 2-aminoadipic acid and gut microbiome derived metabolites.

Amino acids include: glycine, phenylalanine, serine, tyrosine; isoleucine; leucine; and valine. Primary bile acid metabolites include: glycocholate, taurocholate, isoursodeoxycholate, glycochenodeoxycholate, and taurochenodeoxycholate.

Gut microbiome derived metabolites include: trimethylamine N-oxide (TMAO), imidazole propionate, 4-ethylphenol, 4-ethylphenylsulfate, 4-hydroxyphenylacetate, 4-hydroxyphenylacrylate, 4-hydroxyphenyllactate, 4-hydroxyphenylpropionate, 4-hydroxyphenylpyruvate, 4-hydroxyphenylacetylglutamine, cinnamoylglycine, p-cresol, p-cresol glucuronide, p-cresol sulfate, phenol, phenol glucuronide, phenol sulfate, phenylacetate, phenylacetylglutamine, phenylacetylgultamate, phenylacetylglycine, phenylacrylate, phenylalanine, phenyllactate (PLA), phenylpropionate, phenylpropionylglycine, phenylpyruvate, p-vinylphenol, p-vinylphenol sulfate, 12-dehydrocholate, chenodeoxycholate, cholate, deoxycholate, hyodeoxycholate, isocholate, lithocholate, ursocholate, ursodeoxycholate, glycohyocholate, acetate, propionate, butyrate, isobutyrate, isovalerate, valerate, capronic acid, 3-hydroxyanthranilate, 3-hydroxykynurenine, 3-indoxyl sulfate, 5-hydroxytryptophan, indole-3-acetamide (IAM), indole-3-lactate (ILA), indole-3-propionate (IPA), indoleacetate (IAA), indoleacetylglutamine, indoleacetylglycine, indoleacrylate (IA), indoleacrylglycine, indoleethanol (IE), kynurenate, kynurenine, melatonin, N-acetylserotonin, quinolinate, 3-hydroxybenzoate, 3-hydroxyhippurate, 3-hydroxyphenylpropionate, benzoate, and hippurate.

Example 1: Collection of Serum Samples

Serum samples of normal pregnant women and GDM were selected. All of he samples are confirmed by gold standard tests There are 60 cases for normal pregnant women (30 samples) and GDM (30 samples), and all are in the mid-term of pregnancy (20-28 weeks).

Example 2: Extraction of Serum Metabolites

Methanol precipitants containing multiple isotope internal standards were added into serum samples according to a ratio of 1:4, and oscillated for 3 min for uniformly mixing, and then the mixture was centrifuged at 4000×g at 20° C. for 10 min. Four parts of supernatant of which each was 100 μL were taken from each sample and put into four sample plates, the supernatants were blown to be dry by nitrogen, and reconstitution solution containing the isotope internal standards was added for subsequent UPLC-MS/MS detection.

Example 3: Detection and Data Preprocessing for Extracted Serum Metabolites (1) Liquid Chromatography/Mass Spectrometry Conditions.

All four UPLC-MS/MS methods were performed using ACQUITY 2D UPLC (Ultra-performance liquid chromatography; Waters, Milford, MA, USA) coupled with Q Exactive (QE) high-resolution mass spectrometry (Thermo Fisher Scientific, San Jose, USA). Mass spectrometry parameters were: scanning resolution: 35,000; scanning range: 70-1,000 m/z. The specific parameters for 4 UPLC-MS/MS methods were as follows:

Method 1: QE was detected by adopting a positive ion electrospray ionization (ESI) mode, a liquid phase was separated by using a C18 chromatographic column (UPLC BEH C18, 2.1×100 mm, 1.7 m; Waters), wherein the mobile phase was water (A) containing 0.05% of PFPA (pentafluoropropionic anhydride) and 0.1% of FA (formic acid) and methanol (B);

Method 2: QE was detected by adopting a negative ion electrospray ionization (ESI) mode, a liquid phase was separated by using a C18 chromatographic column (UPLC BEH C18, 2.1×100 mm, 1.7 m; Waters), wherein the mobile phase was water (A) containing 6.5 mM ammonium bicarbonate and methanol (B);

Method 3: QE was detected by adopting a positive ion electrospray ionization (ESI) mode, a liquid phase was separated by using a C18 chromatographic column (UPLC BEH C18, 2.1×100 mm, 1.7 m; Waters), wherein the mobile phase was water (A) containing 0.05% PFPA and 0.1% FA and methanol (B);

Method 4: QE was detected by adopting a negative ion electrospray ionization (ESI) mode, a liquid phase was separated by using a HILIC chromatographic column (UPLC BEH Amide, 2.1×150 mm, 1.7 m; Waters), wherein the mobile phase was water (A) containing 10 mM ammonium formate and methanol (B).

(2) Data Preprocessing

After the original peak area of each metabolite was obtained, standardization processing was carried out for subsequent statistics and physiological analysis. Firstly, logarithmic transformation (log 2) with the base number being 2 was carried out on the original peak area of each metabolite so as to reduce the skewness distribution of the overall value and enable data to be close to normal distribution, then normalization was carried out by using the median, and finally the minimum value of all samples was used for imputing the missing value.

Figure 4A:
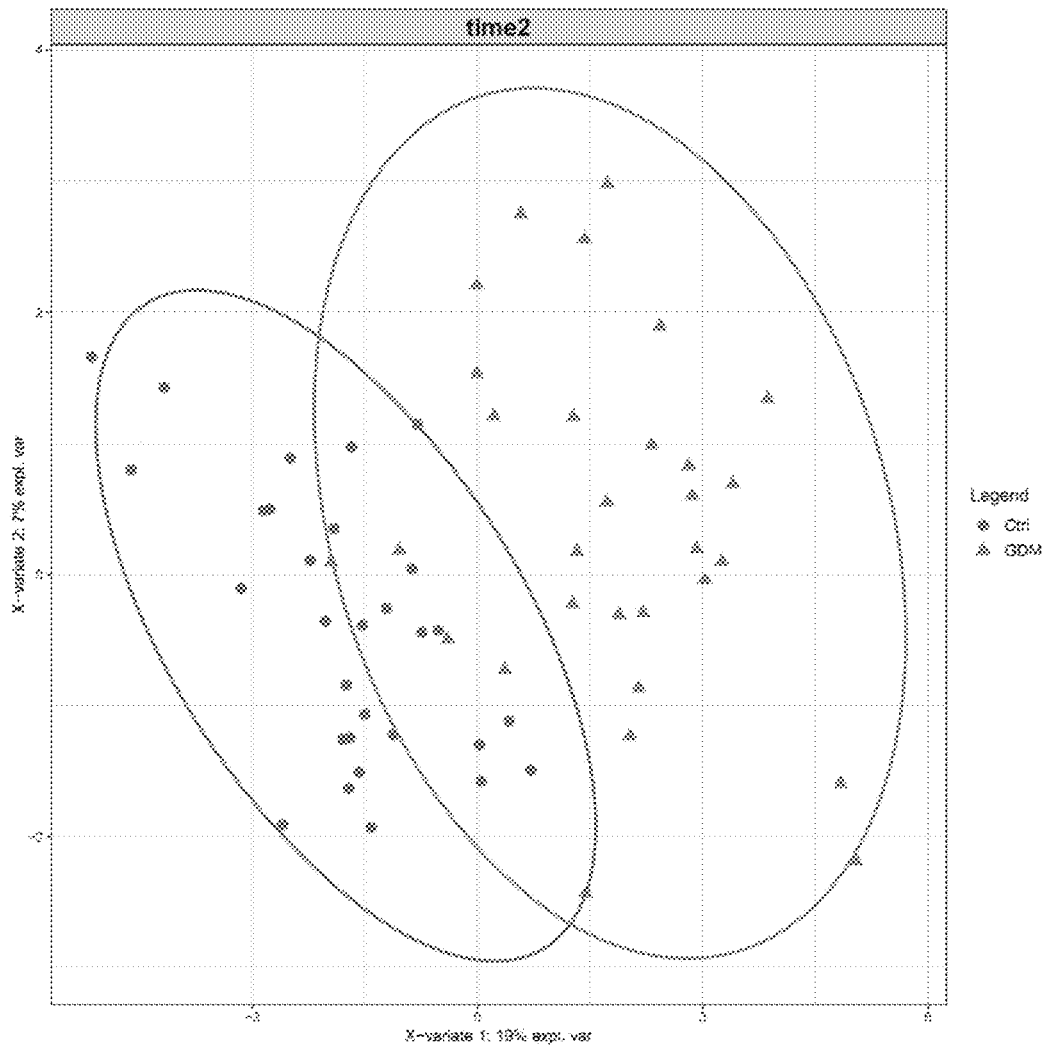
FIG. 4 is an OPLS-DA statistical result of normal pregnant women (CM) group and Pregnant women with GDM (GDM) group (the right FIG. 4A shows the results of 19 biomarkers and the left FIG. 4B shows the results of 48 biomarkers).
Figure 4B:
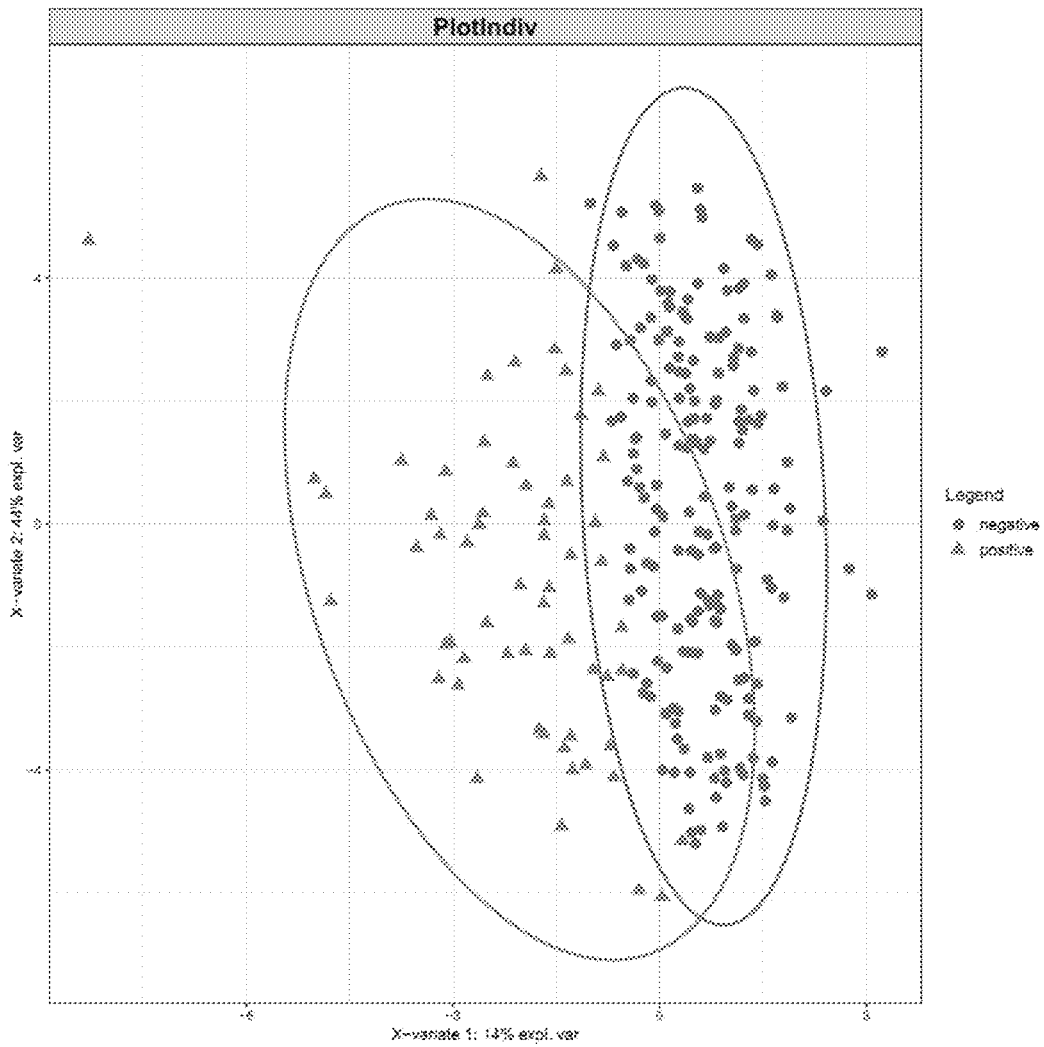

Example 4: Sample Grouping by Orthogonal Partial Least Squares Discriminant Analysis and Differential Metabolites Screening with Significance Analysis Metabolomics generally adopted a mode of combining univariate analysis and multivariate statistical analysis to screen differential metabolites, wherein the univariate analysis mainly comprised significance analysis (p value or FDR value) and fold change of characteristic ions in different groups; and the multivariate statistical analysis mainly comprised Principal Component Analysis (PCA), partial least squares discriminant analysis (PLS-DA), orthogonal partial least squares discriminant analysis (OPLS-DA), etc., as shown in FIG. 4.

All statistical analyses were done using R, and the specific R-related information was shown in Table 1 below.

TABLE 1

| R used in the present invention and related information | |
|---|---|
| Name | Version |
| R | 3.4.1 |
| Rstudio | 1.4.1717 |
| mixOmics | 6.10.9 |
| ropls | 1.18.1 |

Variable Importance for the Projection (VIP) was calculated to measure the influence intensity and the interpretation ability of the expression pattern of each metabolite on the classification and discrimination of each group of samples, and Wilcoxon rank sum test was further carried out to obtain corrected p value (FDR).

According to the screening criteria of the differential metabolites: (1) VIP>1, (2) FDR<0.05, namely, when VIP>1 or FDR<0.05, the metabolites were determined to have significant differences between two groups, and the metabolites were the differential metabolites between the two groups.

The present invention found that the main significant differential metabolites were:

TABLE 2

| Differential metabolites between pregnant women with GDM and normal pregnant women | | | | |
|---|---|---|---|---|
| Serial number | Name | FDR | VIP | Related metabolic pathways |
| 1 | (R)-3-hydroxybutyrylcarnitine | 0.016 | 0.879 | Fatty Acid Metabolism (Acyl Carnitine, Hydroxy) |
| 2 | 1,5-anhydroglucitol (1,5-AG) | 0.025 | 1.079 | Glycolysis, Gluconeogenesis, and Pyruvate Metabolism |
| 3 | 1-arachidonoyl-GPC (20:4) | 0.029 | 1.103 | Lysophospholipid |
| 4 | 1-arachidonoyl-GPI (20:4) | 0.008 | 1.041 | Lysophospholipid |
| 5 | 1-linoleoyl-GPC (18:2) | 0.007 | 1.129 | Lysophospholipid |
| 6 | 1-palmitoyl-GPA (16:0) | 0.010 | 0.896 | Lysophospholipid |
| 7 | 1-palmitoyl-GPC (16:0) | 0.008 | 0.339 | Lysophospholipid |
| 8 | 2-aminoadipic acid | 0.044 | 1.359 | Lysine Metabolism |
| 9 | 2-hydroxybutyrate (AHB) | 0.008 | 2.560 | Glutathione Metabolism |
| 10 | 3-(4-hydroxyphenyl)lactate (HPLA) | 0.030 | 0.890 | Tyrosine Metabolism |
| 11 | 3-hydroxybutyrate (BHBA) | 0.035 | 0.366 | Ketone Bodies |
| 12 | 3-methyl-2-oxobutyrate | 0.043 | 1.233 | Leucine, Isoleucine and Valine Metabolism |

TABLE 2-continued

Differential metabolites between pregnant women with GDM and normal pregnant women

| Serial number | Name | FDR | VIP | Related metabolic pathways |
|---|---|---|---|---|
| 13 | 3-methyl-2-oxovalerate | 0.009 | 0.459 | Leucine, Isoleucine and Valine Metabolism |
| 14 | 4-methyl-2-oxopentanoate | 0.008 | 0.499 | Leucine, Isoleucine and Valine Metabolism |
| 15 | 8-methoxykynurenate | 0.009 | 0.942 | Tryptophan Metabolism |
| 16 | carnitine | 0.005 | 0.889 | Carnitine Metabolism |
| 17 | cis-3,4-methyleneheptanoylcarnitine | 0.017 | 0.902 | Fatty Acid Metabolism (Acyl Carnitine, Hydroxy) |
| 18 | cystathionine | 0.012 | 0.880 | Methionine, Cysteine, SAM (S-Adenosylmethionine) and Taurine Metabolism |
| 19 | cysteinylglycine disulfide | 0.009 | 0.879 | Glutathione Metabolism |
| 20 | deoxycholate | 0.006 | 0.884 | Secondary Bile Acid Metabolism |
| 21 | γ-glutamyl-epsilon-lysine | 0.007 | 0.915 | γ-glutamyl Amino Acid |
| 22 | glucose | 0.022 | 2.058 | Glycolysis, Gluconeogenesis, and Pyruvate Metabolism |
| 23 | glycerophosphoinositol | 0.009 | 0.937 | Phospholipid Metabolism |
| 24 | glycine | 0.010 | 0.845 | Glycine, Serine and Threonine Metabolism |
| 25 | glycocholenate sulfate | 0.005 | 0.887 | Secondary Bile Acid Metabolism |
| 26 | glycolithocholate sulfate | 0.034 | 0.882 | Secondary Bile Acid Metabolism |
| 27 | histidylalanine | 0.009 | 0.970 | Dipeptide |
| 28 | indolelactate | 0.005 | 1.016 | Tryptophan Metabolism |
| 29 | isoleucine | 0.008 | 0.293 | Leucine, Isoleucine and Valine Metabolism |
| 30 | isoursodeoxycholate sulfate (2) | 0.005 | 0.965 | Secondary Bile Acid Metabolism |
| 31 | isovalerate (C5) | 0.042 | 0.908 | Leucine, Isoleucine and Valine Metabolism |
| 32 | lanthionine | 0.009 | 0.932 | Methionine, Cysteine, SAM and Taurine Metabolism |
| 33 | leucine | 0.008 | 0.275 | Leucine, Isoleucine and Valine Metabolism |
| 34 | N6-acetyllysine | 0.005 | 0.926 | Lysine Metabolism |
| 35 | N-acetyltaurine | 0.010 | 1.354 | Methionine, Cysteine, SAM and Taurine Metabolism |
| 36 | N-acetyltryptophan | 0.006 | 1.201 | Tryptophan Metabolism |
| 37 | N-acetylvaline | 0.047 | 0.886 | Leucine, Isoleucine and Valine Metabolism |
| 38 | oleate | 0.010 | 0.015 | Long Chain Monounsaturated Fatty Acid |
| 39 | orotidine | 0.026 | 0.906 | Pyrimidine Metabolism, Orotate containing |
| 40 | oxalate (ethanedioate) | 0.025 | 1.245 | Ascorbate and Aldarate Metabolism |
| 41 | palmitoylcarnitine | 0.060 | 0.770 | Fatty Acid Metabolism (Acyl Carnitine, Long Chain Saturated) |
| 42 | pantothenic acid | 0.019 | 1.088 | Pantothenate and CoA Metabolism |
| 43 | phenylalanine | 0.009 | 0.100 | Phenylalanine, tyrosine and tryptophan biosynthesis; Phenylalanine metabolism |
| 44 | pyroglutamine | 0.006 | 0.915 | Glutamate Metabolism |
| 45 | (Serine) | 0.008 | 0.801 | Glycine, Serine Metabolism |
| 46 | threonate | 0.018 | 0.945 | Ascorbate and Aldarate Metabolism |
| 47 | tyrosine | 0.007 | 0.292 | Tyrosine Metabolism |
| 48 | valine | 0.034 | 0.004 | Leucine, Isoleucine and Valine Metabolism |

48 serum differential metabolites or biomarkers between GDM and normal pregnant women in the above table could be used as candidate biomarkers for differential diagnosis of GDM or not. One or a combination of the 48 serum metabolites could be selected for auxiliary diagnosis of GDM. The smaller the FDR value and/or the larger the VIP value in the table were/was, the more significant the difference of the differential compounds between two groups was to a certain extent, and meanwhile, the differential compounds might have higher diagnostic value. It could be known from the above table that the 48 differential metabolites were mainly related to metabolic pathways such as carbohydrate metabolism, fatty acid metabolism, phospholipid metabolism and amino acid metabolism, a certain compound or metabolite on the related metabolic pathway had difference, and the difference might affect other metabolites on the metabolic pathway, so that the biomarkers of GDM could be further found on the metabolic pathways.

Example 5: Classification Model for Identifying and Diagnosing Pregnant Women with GDM and Normal Pregnant Women and Establishment 1. A Classification Model for Identifying and Diagnosing Pregnant Women with GDM and Normal Pregnant Women Through a Single Differential Metabolite.

An ROC curve of each metabolite in Table 3 of Example 4 was established, and the size of the area under the curve (AUC) was used to judge the pros and cons of the experimental results. An AUC of 0.5 indicated that a single metabolite had no diagnostic value; AUC greater than 0.5 indicated that a single metabolite had diagnostic value. The higher the AUC, the higher the diagnostic value of a single metabolite.

TABLE 3

ROC analysis of ROC values and related information of different metabolites in samples from GDM and normal pregnant women

| Serial number | Metabolites | AUC | 95% confidence interval | Sensitivity | Specficity | Cut-off value |
|---|---|---|---|---|---|---|
| 1114 | deoxycholate | 0.649 | −0.398~0.056 | 0.550 | 0.550 | 1.003 |
| 1591 | N-acetylvaline | 0.678 | −0.126~0.007 | 0.517 | 0.517 | 0.987 |
| 15500 | carnitine | 0.660 | 0.21~0.349 | 0.517 | 0.517 | 1.000 |
| 15705 | cystathionine | 0.667 | −0.904~−0.427 | 0.583 | 0.583 | 0.852 |
| 18349 | indolelactate | 0.697 | −0.137~0.032 | 0.567 | 0.567 | 0.994 |
| 20694 | oxalate (ethanedioate) | 0.727 | 0.057~0.236 | 0.617 | 0.617 | 1.002 |
| 27738 | threonate | 0.686 | 0.094~0.344 | 0.600 | 0.600 | 1.000 |
| 32197 | 3-(4-hydroxyphenyl)lactate (HPLA) | 0.697 | −0.117~0.071 | 0.583 | 0.583 | 1.003 |
| 32599 | glycocholenate sulfate | 0.664 | 0.089~0.373 | 0.533 | 0.533 | 1.000 |
| 32620 | glycolithocholate sulfate | 0.646 | −0.44~0.129 | 0.533 | 0.533 | 1.016 |
| 33228 | 1-arachidonoyl-GPC (20:4) | 0.690 | −0.091~0.111 | 0.567 | 0.567 | 0.998 |
| 33934 | γ-glutamyl-epsilon-lysine | 0.699 | −0.134~0.009 | 0.567 | 0.567 | 1.000 |
| 33959 | N-acetyltryptophan | 0.724 | −0.031~0.154 | 0.600 | 0.600 | 1.001 |
| 34214 | 1-arachidonoyl-GPI (20:4) | 0.678 | −0.26~−0.009 | 0.550 | 0.550 | 1.001 |
| 34419 | 1-linoleoyl-GPC (18:2) | 0.714 | −0.175~−0.003 | 0.617 | 0.617 | 0.996 |
| 34428 | 1-palmitoyl-GPA (16:0) | 0.596 | −2.305~−1.086 | 0.517 | 0.517 | 0.938 |
| 35172 | orotidine | 0.666 | −0.244~−0.093 | 0.550 | 0.550 | 0.999 |
| 36752 | N6-acetyllysine | 0.654 | −0.12~−0.035 | 0.517 | 0.517 | 1.001 |
| 42002 | lanthionine | 0.684 | −0.516~−0.059 | 0.533 | 0.533 | 0.835 |
| 42027 | histidylalanine | 0.657 | −0.846~−0.354 | 0.567 | 0.567 | 0.276 |
| 43264 | (R)-3-hydroxybutyrylcarnitine | 0.654 | 0.02~0.915 | 0.633 | 0.633 | 0.650 |
| 44656 | isovalerate (C5) | 0.680 | −0.041~0.188 | 0.550 | 0.550 | 1.003 |
| 46225 | pyroglutamine | 0.687 | −0.085~0.181 | 0.633 | 0.633 | 1.004 |
| 47155 | glycerophosphoinositol | 0.700 | −0.606~0.201 | 0.567 | 0.567 | 0.996 |
| 48187 | N-acetyltaurine | 0.773 | −0.108~0.077 | 0.650 | 0.650 | 0.996 |
| 62103 | cysteinylglycine disulfide | 0.690 | 0.152~0.335 | 0.583 | 0.567 | 0.992 |
| 62955 | 8-methoxykynurenate | 0.690 | −0.171~0.204 | 0.550 | 0.550 | 0.961 |
| 63603 | isoursodeoxycholate sulfate (2) | 0.711 | −0.522~0.125 | 0.600 | 0.600 | 0.666 |
| 64389 | cis-3,4-methyleneheptanoylcarnitine | 0.662 | −0.045~0.291 | 0.583 | 0.583 | 0.997 |
| M-1 | glucose | 0.799 | −1.815~−0.977 | 0.727 | 0.725 | 0.124 |
| M-10 | palmitoylcarnitine | 0.627 | −1.001~−0.284 | 0.636 | 0.647 | −0.694 |
| M-11 | oleate | 0.527 | −0.662~0.11 | 0.523 | 0.521 | −0.343 |
| M-12 | glycine | 0.627 | 0.374~1.053 | 0.636 | 0.635 | 0.128 |
| M-13 | phenylalanine | 0.512 | −0.285~0.371 | 0.523 | 0.527 | −0.026 |
| M-14 | serine | 0.631 | 0.068~0.81 | 0.568 | 0.557 | 0.079 |
| M-15 | tyrosine | 0.573 | −0.032~0.6 | 0.568 | 0.569 | 0.092 |
| M-16 | isoleucine | 0.532 | −0.149~0.492 | 0.500 | 0.509 | 0.033 |
| M-17 | leucine | 0.542 | −0.09~0.537 | 0.500 | 0.503 | −0.066 |
| M-18 | valine | 0.509 | −0.193~0.497 | 0.523 | 0.527 | 0.016 |
| M-19 | 2-aminoadipic acid | 0.691 | −0.857~−0.171 | 0.614 | 0.617 | −0.079 |
| M-2 | 1,5-anhydroglucitol (1,5-AG) | 0.694 | 0.244~0.773 | 0.614 | 0.611 | −0.020 |
| M-3 | 3-methyl-2-oxobutyrate | 0.691 | −0.97~−0.261 | 0.636 | 0.635 | 0.147 |
| M-4 | 3-hydroxybutyrate (BHBA) | 0.569 | −1.141~−0.151 | 0.568 | 0.575 | −0.371 |
| M-5 | 2-hydroxybutyrate (AHB) | 0.903 | −1.797~−1.137 | 0.818 | 0.820 | 0.324 |
| M-6 | pantothenic acid | 0.664 | −1.24~−0.316 | 0.614 | 0.611 | −0.367 |
| M-7 | 3-methyl-2-oxovalerate | 0.593 | −0.505~−0.139 | 0.568 | 0.569 | 0.141 |
| M-8 | 4-methyl-2-oxopentanoate | 0.572 | −0.526~−0.13 | 0.545 | 0.545 | 0.034 |
| M-9 | 1-palmitoyl-GPC (16:0) | 0.557 | −0.649~0.086 | 0.568 | 0.569 | 0.047 |

2. A Classification Model for Identifying and Diagnosing Pregnant Women with GDM and Normal Pregnant Women Through a Combination of Multiple Differential Metabolites.

Based on the relative abundance of differential metabolites in Table 3 in GDM and normal pregnant women, a model for identifying and diagnosing pregnant women with GDM and normal pregnant women was established by using orthogonal partial least squares regression (Rstudio software, NIPALS algorithm implementation) (19 metabolite variables formed an independent variable matrix, and logic values of "pregnant women with GDM" and "normal pregnant women" were used as dependent variables), variable projection importance (VTP), FDR values, etc. were calculated to measure the influence intensity and interpretation ability of the expression mode of each metabolite on classification and discrimination of each group of samples, Wilcoxon rank sum test was further performed to obtain a corrected p value (FDR), and optimal model parameters (Rstudio software) for identifying and diagnosing GDM were screened to obtain a prediction model A and a prediction model B.

19 differential metabolites were selected to establish a model A, and the model variables and related parameters were shown in Table 4 below:

TABLE 4

List of variables and parameters of model A

| Serial number | Model variables | Model coefficients | Standard error | Significant p | Odds ratio (OR) |
|---|---|---|---|---|---|
| M-1 | glucose | 3.425 | 0.008 | 0.043 | 30.723 |
| M-10 | palmitoylcarnitine | 0.854 | 0.009 | 0.008 | 2.348 |
| M-11 | oleate | −4.598 | 0.010 | 0.039 | 0.010 |
| M-12 | glycine | −1.307 | 0.018 | 0.018 | 0.271 |
| M-13 | phenylalanine | 0.309 | 0.007 | 0.009 | 1.361 |
| M-14 | serine | −2.253 | 0.009 | 0.005 | 0.105 |
| M-15 | tyrosine | −0.335 | 0.010 | 0.028 | 0.715 |
| M-16 | isoleucine | −0.172 | 0.108 | 0.037 | 0.842 |
| M-17 | leucine | −1.273 | 0.090 | 0.029 | 0.280 |
| M-18 | valine | −0.422 | 0.017 | 0.036 | 0.656 |
| M-19 | 2-aminoadipic acid | 0.622 | 0.005 | 0.033 | 1.862 |
| M-2 | 1,5-anhydroglucitol (1,5-AG) | −0.882 | 0.004 | 0.034 | 0.414 |
| M-3 | 3-methyl-2-oxobutyrate | 0.898 | 0.008 | 0.007 | 2.454 |
| M-4 | 3-hydroxybutyrate (BHBA) | 2.292 | 0.012 | 0.017 | 9.892 |
| M-5 | 2-hydroxybutyrate (AHB) | 2.919 | 0.004 | 0.044 | 18.528 |
| M-6 | pantothenic acid | 1.319 | 0.006 | 0.039 | 3.741 |
| M-7 | 3-methyl-2-oxovalerate | −0.103 | 0.088 | 0.034 | 0.902 |
| M-8 | 3-methyl-2-oxovalerate | 0.856 | 0.054 | 0.048 | 2.353 |
| M-9 | 1-palmitoyl-GPC (16:0) | 1.256 | 0.018 | 0.009 | 3.512 |

Model A equation was: Score=3.425*glucose+0.854*palmitoylcarnitine−4.598*oleate−1.307*glycine+0.309*phenylalanine−2.253*Serine−0.335*tyrosine−0.172*isoleucine−1.273*leucine−0.422*valine+0.622*20aminoadipic acid−0.882*1,5-anhydroglucitol (1,5-AG)+5.898*3-methyl2-oxobutyrate+2.292*32hydroxybutyrate (B2BA)+2.919*2hydroxybutyrate (AB)+1.319*pantothenic acid−0.103*3-methyl-2-oxovalerate+0.856*4-methyl(2hoxopentanoate+1.256*1-palmitoyl-GPC (16:0).

Figure 5:
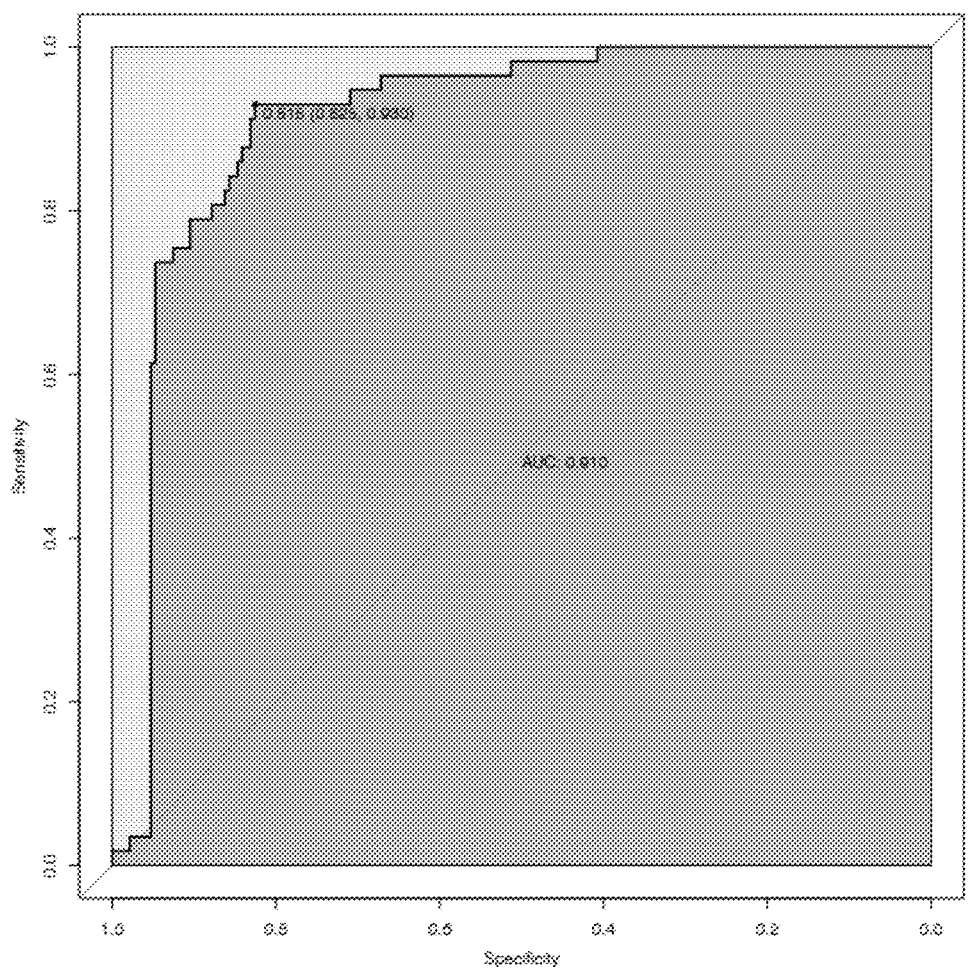
FIG. 5 is a ROC curve for model A.

In the model equation, names such as glucose and 1,5-Hydroglucitol represented the relative abundance of corresponding biomarkers. As shown in FIG. 5, ROC analysis was performed, AUC was 0.910, and Sensitivity and Specificity were 0.825 and 0.930 respectively, which indicated that the model A could be used for differential diagnosis of pregnant women with GDM and normal pregnant women. The critical value of the model A was 0.515, the relative abundance of each biomarker was substituted into the equation, and when Score was >0.515, the probability of diagnosing GDM was very high; and when Score was ≤0.515, the probability of diagnosing GDM was low.

48 differential metabolites were selected to establish a model B, and the model variables and related parameters were shown in Table 5.1 below:

TABLE 5.1

List of variables and parameters of model B

| Serial number | Model variables(CAScode) | Model coefficients | Standard error | Significant p | Odds ratio (OR) |
|---|---|---|---|---|---|
| 1114 | Deoxycholate (83-44-3) | 0.199 | 0.690 | 0.028 | 1.220 |
| 1591 | N-acetylvaline (96-81-1) | 2.903 | 2.435 | 0.017 | 18.229 |
| 15500 | Carnitine (541-15-1) | 4.004 | 2.226 | 0.011 | 54.817 |
| 15705 | Cystathionine (56-88-2) | −1.611 | 0.846 | 0.010 | 0.200 |
| 18349 | Indolelactate (1821-52-9) | 2.441 | 2.178 | 0.023 | 11.483 |
| 20694 | oxalate (ethanedioate)( 144-62-7) | −1.765 | 3.569 | 0.037 | 0.171 |
| 27738 | Threonate(7306-96-9) | −1.271 | 2.801 | 0.047 | 0.281 |
| 32197 | 3-(4-hydroxyphenyl)lactate (HPLA) (306-23-0) | −0.588 | 1.713 | 0.015 | 0.556 |
| 32599 | glycocholenate sulfate(Not Available) | 0.284 | 0.924 | 0.039 | 1.329 |
| 32620 | glycolithocholate sulfate(15324-64-8) | −0.678 | 0.597 | 0.049 | 0.508 |
| 33228 | 1-arachidonoyl-GPC (20:4)( 60701-99-7) | −4.844 | 1.678 | 0.029 | 0.008 |
| 33934 | γ-glutamyl-epsilon-lysine(17105-15-6) | 4.307 | 2.131 | 0.041 | 74.233 |
| 33959 | N-acetyltryptophan(1218-34-4) | −1.769 | 2.125 | 0.004 | 0.170 |
| 34214 | 1-arachidonoyl-GPI (20:4) (1246430-04-5) | −0.495 | 1.719 | 0.022 | 0.610 |
| 34419 | 1-linoleoyl-GPC (18:2) (22252-07-9) | 2.144 | 2.302 | 0.023 | 8.530 |
| 34428 | 1-palmitoyl-GPA (16:0) (17618-08-5) | 0.635 | 0.261 | 0.018 | 1.886 |
| 35172 | Orotidine(314-50-1) | 0.171 | 1.950 | 0.038 | 1.186 |
| 36752 | N6-acetyllysine(692-04-6) | −4.154 | 3.581 | 0.015 | 0.016 |
| 42002 | Lanthionine(3183-08-2) | −0.039 | 0.544 | 0.010 | 0.961 |
| 42027 | Histidylalanine(16874-75-2) | 0.893 | 0.652 | 0.035 | 2.444 |
| 43264 | (R)-3-hydroxybutyrylcarnitine(Not Available) | 0.995 | 0.411 | 0.041 | 2.705 |
| 44656 | isovalerate (C5) (503-74-2) | 0.756 | 1.276 | 0.045 | 2.131 |
| 46225 | pyroglutamine2353-44-8 | −1.463 | 1.154 | 0.047 | 0.232 |
| 47155 | Glycerophosphoinositol(16824-65-0) | −0.503 | 0.560 | 0.047 | 0.605 |
| 48187 | N-acetyltaurine(19213-70-8) | −0.513 | 1.692 | 0.039 | 0.598 |
| 62103 | cysteinylglycine disulfide(70555-24-7) | 0.205 | 1.890 | 0.042 | 1.228 |
| 62955 | 8-methoxykynurenate2929-14-8 | −1.874 | 0.826 | 0.018 | 0.154 |
| 63603 | isoursodeoxycholate sulfate (2) (Not Available) | 0.361 | 0.461 | 0.029 | 1.435 |
| 64389 | cis-3,4-methyleneheptanoylcarnitine (Not Available) | −1.421 | 0.814 | 0.024 | 0.242 |
| M-1 | Glucose (50-99-7) | 3.425 | 0.008 | 0.043 | 30.723 |
| M-10 | Palmitoylcarnitine (2364-67-2) | 0.854 | 0.009 | 0.008 | 2.348 |
| M-11 | oleate (115-06-0) | −4.598 | 0.010 | 0.039 | 0.010 |
| M-12 | Glycine (56-40-6) | −1.307 | 0.018 | 0.018 | 0.271 |
| M-13 | Phenylalanine (63-91-2) | 0.309 | 0.007 | 0.009 | 1.361 |
| M-14 | Serine (56-45-1) | −2.253 | 0.009 | 0.005 | 0.105 |
| M-15 | Tyrosine (60-18-4) | −0.335 | 0.010 | 0.028 | 0.715 |
| M-16 | Isoleucine (73-32-5) | −0.172 | 0.108 | 0.037 | 0.842 |
| M-17 | Leucine (61-90-5) | −1.273 | 0.090 | 0.029 | 0.280 |
| M-18 | Valine (72-18-4) | −0.422 | 0.017 | 0.036 | 0.656 |
| M-19 | 2-aminoadipic acid (7620-28-2) | 0.622 | 0.005 | 0.033 | 1.862 |
| M-2 | 1,5-anhydroglucitol (1,5-AG) (154-58-5) | −0.882 | 0.004 | 0.034 | 0.414 |
| M-3 | 3-methyl-2-oxobutyrate (3715-29-5) | 0.898 | 0.008 | 0.007 | 2.454 |
| M-4 | 3-hydroxybutyrate (BHBA) ( 300-85-6) | 2.292 | 0.012 | 0.017 | 9.892 |
| M-5 | 2-hydroxybutyrate (AHB) (600-15-7) | 2.919 | 0.004 | 0.044 | 18.528 |
| M-6 | pantothenic acid (79-83-4) | 1.319 | 0.006 | 0.039 | 3.741 |
| M-7 | 3-methyl-2-oxovalerate (1460-34-0) | −0.103 | 0.088 | 0.034 | 0.902 |
| M-8 | 4-methyl-2-oxopentanoate (816-66-0) | 0.856 | 0.054 | 0.048 | 2.353 |
| M-9 | 1-palmitoyl-GPC (16:0) (17364-16-8) | 1.256 | 0.018 | 0.009 | 3.512 |

Model B equation was: Score=−0.0199*deoxycholate−0.290*N-acetylvaline−0.400*carnitine+0.161*cystathionine−0.244*indolelactate+0.177*oxalate (ethanedioate)+0.127*threonate+0.00588*3-(4-hydroxyphenyl)lactate (TIPLA)−0.0284*glycocholenate sulfate+0.0678*glycolithocholate sulfate+0.484*1-arachidonoyl-GPC (20:4)−0.431*γ-glutamyl-epsilon-lysine+0.177*N-acetyltryptophan+0.0495*1-arachidonoyl-GPI (20:4)−0.214*1-linoleoyl-GPC (18:2)−0.0635*1-palmitoyl-GPA (16:0)−0.0171*orotidine+0.415*N6-acetyllysine+0.0039*lanthionine−0.0893*histidylalanine−0.0995*(R)-3-hydroxybutyrylcarnitine−0.0756*isovalerate (C5)+0.146*pyroglutamine+0.0503*glycerophosphoinositol+0.0513*N-acetyltaurine−0.0205*cysteinylglycine disulfide+0.187*8-methoxykynurenate−0.0361*<isoursodeoxycholate sulfate (2)+0.142*cis-3,4-methyleneheptanoylcarnitine.

Figure 6:
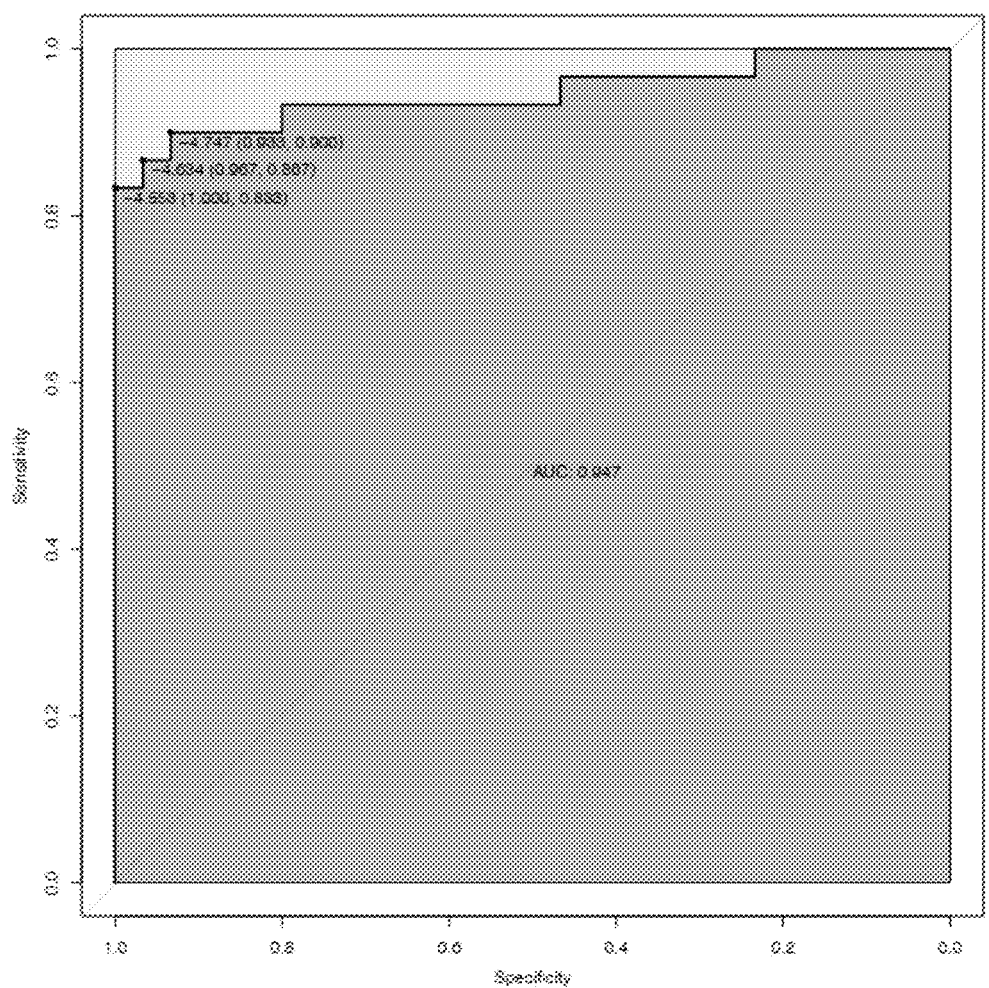
FIG. 6 is a ROC curve for model B.

As shown in FIG. 6, ROC analysis was performed, the AUC of model B was 0.947, the sensitivity and specificity were 0.967 and 0.867 respectively, which indicated that the model B could be used for differential diagnosis of pregnant women with GDM and normal pregnant women. The critical value of the model B was 0.463 (cut-off value), the relative abundance of each biomarker was substituted into the equation, and when Score was >0.463, the probability of diagnosing GDM was very high; and when Score was ≤0.463, the probability of diagnosing GDM was low.

TABLE 5

2 List of metabolites with the construction (cade is not Available)

| Serial number | name | CAS code | Formula | construction |
|---|---|---|---|---|
| 32599 | glycocholenate sulfate | Not Available | C26H41NO9S | |
| 43264 | (R)-3-hydroxy-butyrylcarnitine | Not Available | C11H21NO5 | |
| 63603 | isoursodeoxycholate sulfate (2) | Not Available | C24H40O7S | |
| 64389 | cis-3,4-methylene-heptanoylcarnitine | Not Available | C15H27NO4 | |

11 differential metabolites were selected to establish a model C, and the model variables and related parameters were shown in Table 6 below:

TABLE 6

List of variables and parameters of model C

| Serial number | Model variables | Model coefficients | Standard error | Significant p | Odds ratio (OR) |
|---|---|---|---|---|---|
| M-10 | palmitoylcarnitine | 1.775 | 0.009 | 0.008 | 5.902 |
| M-11 | oleate | 0.455 | 0.010 | 0.039 | 1.576 |
| M-12 | glycine | −0.723 | 0.018 | 0.018 | 0.485 |
| M-13 | phenylalanine | 0.203 | 0.007 | 0.009 | 1.225 |
| M-14 | Serine | 0.085 | 0.009 | 0.005 | 1.089 |
| M-15 | tyrosine | −1.599 | 0.010 | 0.028 | 0.202 |
| M-16 | isoleucine | −0.271 | 0.108 | 0.037 | 0.762 |
| M-17 | leucine | −1.177 | 0.090 | 0.029 | 0.308 |
| M-18 | valine | 0.506 | 0.017 | 0.036 | 1.659 |
| M-19 | 2-aminoadipic acid | 1.622 | 0.005 | 0.033 | 5.062 |
| M-9 | 1-palmitoyl-GPC (16:0) | 0.163 | 0.018 | 0.009 | 1.177 |

Model C equation was: Score=1-palmitoyl-GPC (16:
0)*0.163+palmitoylcarnitine*1.775+
oleate*0.455−glycine*0.723+phenylala-
nine*0.203+Serine*0.085−tyrosine*1.599−
isoleucine*0.271−leucine*1.177+valine*0.506+
2-aminoadipic acid*1.622.

Figure 7:
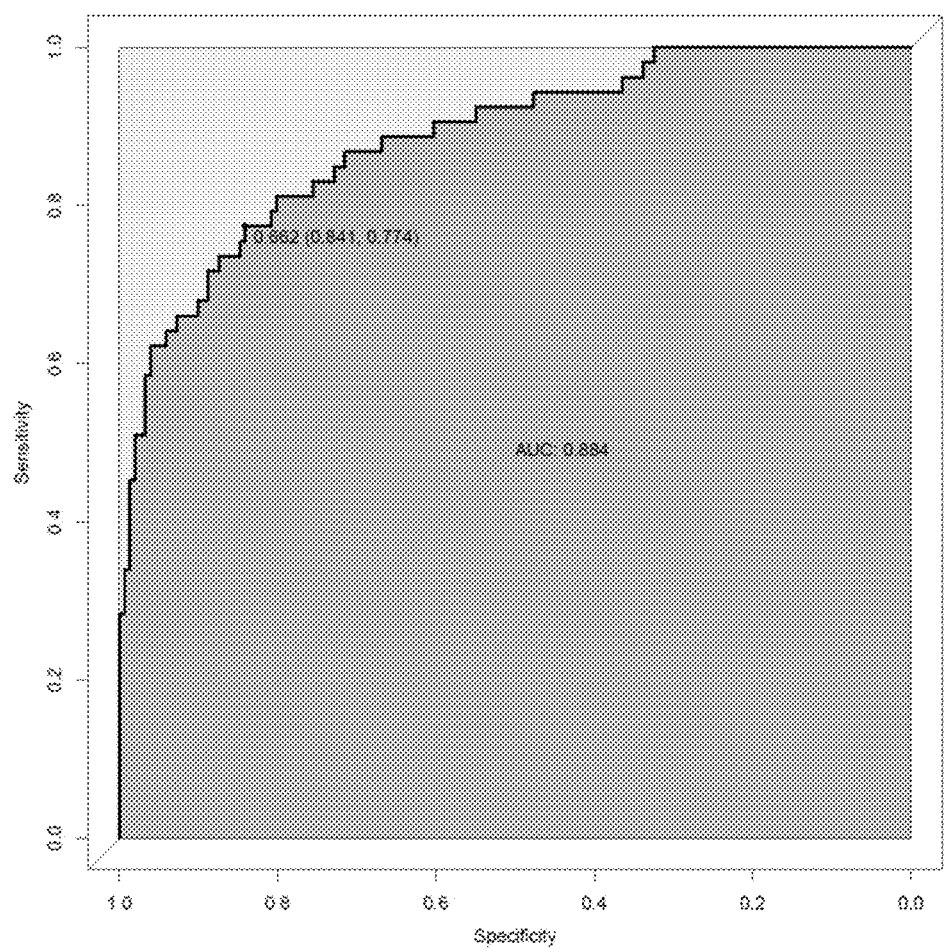
FIG. 7 ROC curve for Model C.

In the model equation, names of biomarkers such as oleate, glycine represented the relative abundance of corresponding biomarkers. As shown in FIG. 7, ROC analysis was performed, the AUC was 0.910, and the sensitivity and specificity were 0.747 and 0.841 respectively, which indicated that the model C could be used for differential diagnosis of pregnant women with GDM and normal pregnant women. The critical value of the model C was 0.662, the relative abundance of each biomarker was substituted into the equation, and when Score was >0.662, the probability of diagnosing GDM was very high; and when Score was ≤0.662, the probability of diagnosing GDM was low.

10 differential metabolites were selected to establish a model D, and the model variables and related parameters were shown in Table 7 below:

TABLE 7

List of variables and parameters of model D

| Serial number | Model variables | Model coefficients | Standard error | Significant p | Odds ratio (OR) |
|---|---|---|---|---|---|
| M-10 | palmitoylcarnitine | 1.847 | 0.009 | 0.008 | 6.340 |
| M-11 | oleate | 0.447 | 0.010 | 0.039 | 1.564 |
| M-12 | glycine | −0.757 | 0.018 | 0.018 | 0.469 |
| M-13 | phenylalanine | 0.235 | 0.007 | 0.009 | 1.265 |
| M-14 | Serine | 0.057 | 0.009 | 0.005 | 1.058 |
| M-15 | tyrosine | −1.606 | 0.010 | 0.028 | 0.201 |
| M-16 | isoleucine | −0.285 | 0.108 | 0.037 | 0.752 |
| M-17 | leucine | −1.103 | 0.090 | 0.029 | 0.332 |
| M-18 | valine | 0.491 | 0.017 | 0.036 | 1.635 |
| M-19 | 2-aminoadipic acid | 1.622 | 0.005 | 0.033 | 5.061 |

Figure 8:
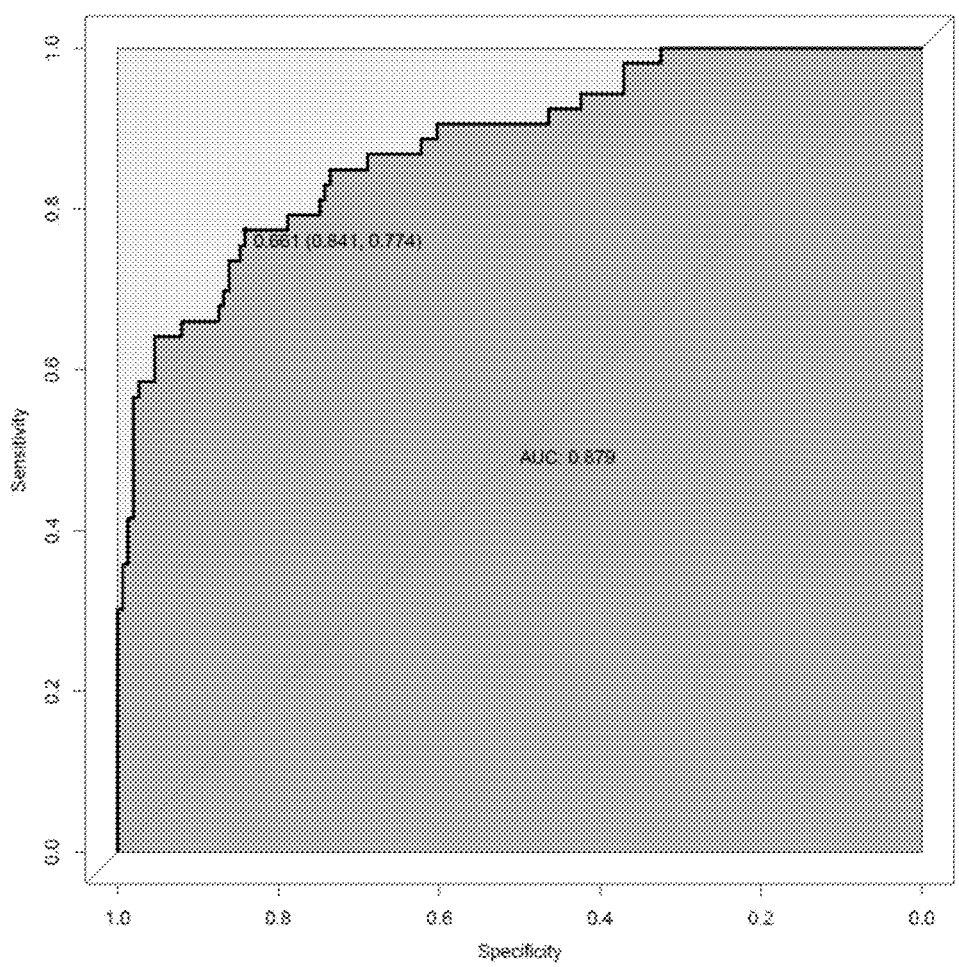
FIG. 8 ROC curve for Model D.

Model D equation was:
Score=1.847*palmitoylcarnitine+0.447*oleate−
0.757*glycine+0.235*phenylalanine+0.057*Ser-
ine−1.606*tyrosine−0.285*isoleucine−
1.103*leucine+0.491*valine+1.622*2-
aminoadipic acid In the model equation, names of biomarkers such as oleate, glycine represented the relative abundance of corresponding biomarkers. Unexpectedly, as shown in FIG. 8, model D could be used for differential diagnosis of pregnant women with GDM and normal pregnant women. That is the ROC analysis of FIG. 8 reveals that the AUC was 0.879, and the sensitivity and specificity were 0.774 and 0.841 respectively. Significantly, the AUC of 0.879 compares very favorably with the model C ROC of 0.661. That is, the probability of diagnosing GDM with model D was very high; while the probability of diagnosing GDM with model C was low. The model D AUC of 0.879 also compares favorably with the AUC in model E of 0.782. An excellent effect was observed in model D, where ten (10) biomarkers gave an AUC of 0.879, whereas in model C, eleven (11) biomarkers gave an AUC of 0.661 and an AUC of 0.782 in model E (nine (9) biomarkers). An advantageous effect was found in model D, where ten (10) biomarkers gave an AUC of 0.879, whereas in model C, eleven (11) biomarkers gave an AUC of 0.661 and an AUC of 0.782 in model E (nine (9) biomarkers).

9 differential metabolites were selected to establish a model E, and the model variables and related parameters were shown in Table 8 below:

TABLE 8

List of variables and parameters of model E

| Serial number | Model variables | Model coefficients | Standard error | Significant p | Odds ratio (OR) |
|---|---|---|---|---|---|
| M-11 | oleate | 0.688 | 0.010 | 0.039 | 1.990 |
| M-12 | glycine | −0.780 | 0.018 | 0.018 | 0.458 |
| M-13 | phenylalanine | 0.484 | 0.007 | 0.009 | 1.623 |
| M-14 | Serine | 0.146 | 0.009 | 0.005 | 1.157 |
| M-15 | tyrosine | −0.781 | 0.010 | 0.028 | 0.458 |
| M-16 | isoleucine | 0.383 | 0.108 | 0.037 | 1.466 |
| M-17 | leucine | −1.431 | 0.090 | 0.029 | 0.239 |
| M-18 | valine | 0.303 | 0.017 | 0.036 | 1.354 |
| M-19 | 2-aminoadipic acid | 1.270 | 0.005 | 0.033 | 3.562 |

Figure 9:
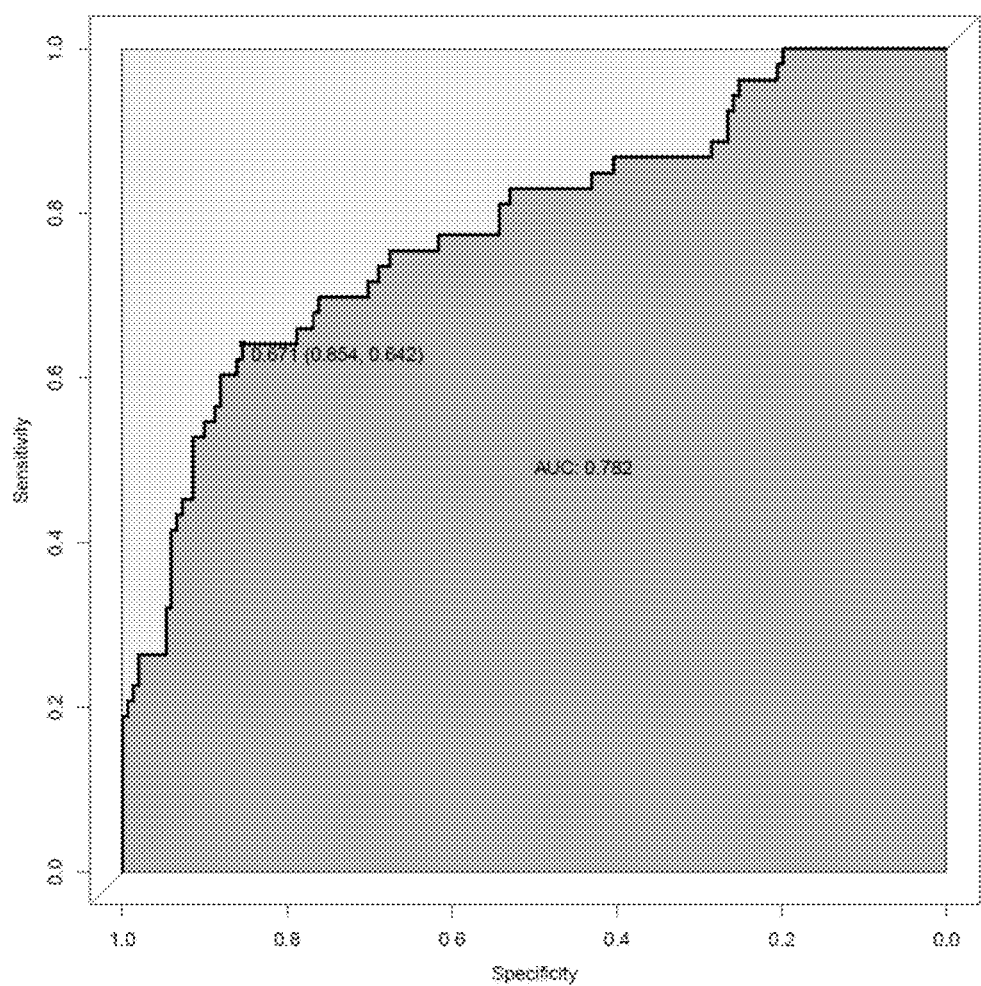
FIG. 9 ROC curve for Model E.

Model E equation was: Score=0.688*oleate−
0.78*glycine+0.484*phenylalanine+0.146*Ser-
ine−0.781*tyrosine+0.383*isoleucine−
1.431*leucine+0.303*valine+1.27*2-
aminoadipic acid In the model equation, names of biomarkers such as oleate, glycine represented the relative abundance of corresponding biomarkers. As shown in FIG. 9, ROC analysis was performed, the AUC was 0.782, and the sensitivity and specificity were 0.642 and 0.854 respectively, which indicated that the model E could be used for differential diagnosis of pregnant women with GDM and normal pregnant women. The critical value of the model C was 0.671, the relative abundance of each biomarker was substituted into the equation, and when Score was >0.671, the probability of diagnosing GDM was very high; and when Score was ≤0.671, the probability of diagnosing GDM was low.

It should be noted that, for any one of the above models, when the model coefficient of a biomarker (or differential metabolite) is a positive number, it indicates that the biomarker is positively correlated with the occurrence of GDM, namely, the greater the relative abundance of the biomarker, the higher the probability of diagnosis of GDM. When the model coefficient is a negative number, it indicates that the biomarker is negatively correlated with GDM, namely, the greater the relative abundance of the biomarker, the lower the possibility of diagnosis of GDM. The higher the absolute value of the model coefficient of the biomarker, the higher the diagnostic value of GDM in the model. For example, in the model A, the model coefficient of oleate is −4.598, and the model coefficient of pantothenic acid is 1.319, indicating that the higher the relative abundance of oleate, the lower the possibility of diagnosis of GDM; and the higher the relative abundance of pantothenic acid, the higher the possibility of diagnosis of GDM. The diagnostic value of oleate is higher than that of pantothenic acid, that is to say, when the relative abundances of oleate and pantothenic acid have the same change, the influence of oleate on the diagnostic results of model A is greater than that of pantothenic acid.

Generally, when establishing a disease diagnosis model, the more biomarkers (or differential metabolites) are selected, the higher the diagnostic accuracy of the model. However, in the actual clinical use, the clinical detection technique, the cost, the interpretation of the clinical report and the complexity of the modeling process need to be considered as well. Therefore, when the accuracy is higher, the model value is not necessarily higher. In addition, when selecting the biomarkers, the metabolic pathways related to the biomarkers should also be considered, including the concentration degree of related metabolic pathways and the interpretability of the biological significance of the pathways, etc. According to a general principle, when a model is use to identify GDM form pergnant women, if it has similar accuracy, the number of the biomarker is reduced that is better. The reasoned is that less number of the biomarkers are used in the model, it is easier to detected with lower cost.

Comparing the above model A, model B, model C, model D and model E, it could be known that:

(1) when the models were established, the selected biomarkers were not necessarily the compounds with higher diagnostic value, for example, the AUC values of N-acetylaurine and phenylalanine in Table 3 were 0.773 and 0.512 respectively, the value of single N-acetylaurine for diagnosing GDM was higher than that of single phenylalanine, but the model A selected phenylalanine as the selected marker and did not select N-acetylaurine.

(2) A biomarker with higher single diagnosis value had different diagnosis values in the model, for example, the AUC values of serine and 2-aminoadipic acid in Table 3 were 0.631 and 0.631 respectively, and the value of single 2-aminoadipic acid for diagnosing GDM was higher than that of single 2-aminoadipic acid; the model coefficient of serine in a model A was −2.253, the model coefficient of 2-aminoadipic acid was 0.622, and the contribution of serine in the model A was far higher than that of 2-aminoadipic acid.

(3) The model B comprised all 48 biomarkers, the AUC value of the model B was 0.947, the sensitivity and specificity of the model B were 0.967 and 0.867 respectively, and the model B had the best diagnostic performance; the model A comprised 19 biomarkers, the AUC value of the model A was 0.910, and the sensitivity and specificity of the model A were 0.825 and 0.930 respectively. The number of the biomarkers of the model A was far lower than that of the biomarkers of the model B, the diagnostic performance was only slightly reduced, and the actual value of the model A was possibly higher than that of the model B due to the fact that the comprehensive detection technology, the detection cost are much more different for model A and model B.

(4) Although the AUC value of the modules C, D and E was lower than that of the model A and that of the model B, the model still had high diagnosis value, the number of biomarkers of the models C, D and E was 11, 10 and 9 respectively, the practical application process was more convenient, and the detection cost was lower.

(5) The model D was 1-palmitoyl-GPC less than the model C, the AUC value of the model D was slightly reduced (from 0.884 to 0.879), and the sensitivity and the specificity of the model D had no obvious change, which indicated that the diagnosis value of the model C had no obvious difference compared with the model D. The model E was palmitoylcarnitine less than the model D, and the AUC value of the model E was obviously reduced (from 0.879 to 0.782), which indicated that the diagnosis value of the model E was lower than that of the model D. Therefore, in comprehensive consideration, in the model with three biomarkers with similar number, the value of the model D was higher.

In order to verify the classification accuracy of the models, a blind selection experiment was used, 150 clinical pregnant women were randomly selected, and the pregnancy time was between 20 weeks and 28 weeks. The abundance value of each marker was tested by adopting the examples of the present invention, and the classification models of models A-E were adopted, and the relative abundance was input by adopting the different markers for identification and classification, so that data which possibly belonged to GDM mellitus was obtained, wherein the number of the models A was 34, the number of the models B was 35, the number of the models C was 36, the number of the models D was 35, and the number of the models E was 38. In the positive GDM mellitus, after the 150 pregnant women were confirmed through the gold standard of diabetes tests, the number of the pregnant women with the GDM was 35 actually. The models were adopted for clearly distinguishing classification prediction, the probability of missed detection or false positive was very low, and the accuracy was more than 97%, so that the classification models established by the markers had certain accuracy and could be used for clinical preliminary classification or identification.

Example 6: Prediction Model for Predicting Blood Glucose Level of Pregnant Women 1. Data Acquisition Data of 499 pregnant women were obtained in total. The data comprised the concentration values (unit: μg/mL) of 19 biomarkers (listed in Table 12) in serum sample measured by liquid chromatography-tandem mass spectrometry. The serum samples are taken at 0 h under fasting sate (without oral glucose taking) and biochemical blood glucose levels (unit: mmol/L, the biochemical blood glucose level was tested by adopting a general kit) at 1 h and 2 h after oh of oral glucose taking (75 g) under fasting state. The detection process of the 19 biomarkers comprised the steps of extracting metabolites in serum samples, detecting by using a liquid chromatography-tandem mass spectrometry, and obtaining the concentration values (specific data summary) of the 19 biomarkers in Table 12, wherein specific sample extraction and processing methods, parameters, etc. could adopt methods introduced in Examples 1-3.

2. Model Establishment

The blood glucose levels of the pregnant individuals at 1 h and 2 h after oral glucose taking under fasting state were the gold standard test (Yang Huixia et al., A new milestone in the diagnostic criteria of GDM, Chinese Journal of Perinatal Medicine, May 2010, Issue 12, Volume 3). We selected 19 biomarkers of GDM to establish a prediction model, brought the measured values of each biomarker at 0 h under fasting (without oral glucose taking) into the prediction model, predicted the blood glucose values at 1 h and 2 h after 0 h, and compared the predicted values with the measured values, so as to judge whether the prediction model was accurate. There is understand that, in our present invention, when use the model to predicted the blood glucose levels, there is no need to oral taking glucose and just take blood sample one time for testing the concentration of the selected biomarkers in this sample.

Firstly, multiple linear regression was considered, and 19 variables (concentration of markers) were brought into a linear regression model, for example, $$Y = \sum_{i=1}^{m} \mu_i \cdot v_i + b$$

where, m was the number of biomarkers, $\mu_i$ was the linear coefficient of the $i^{th}$ biomarker, $v_i$ was the detection value of the $i^{th}$ biomarker (the concentration of 19 markers tested by adopting blood sample under fasting sate), and b was a constant.

Two linear regression models (not shown) respectively used for predicting the blood glucose level at 1 h and 2 h after 0 h under the fasting state were obtained through testing and multiple optimizations of parameters, but the blood glucose level at 1 h and 2 h after 0 h under fasting state predicted by the two models had a large difference from an actually measured value. The R-squared values were 0.32 (1 h) and 0.36 (2 h), the RMSE was 1.32 (1 h) and 1.15 (2 h) for these two line arregression models, and the requirements of clinical modeling were not met and not useful. The general evaluation basis was that the larger the R-squared value was, the better the evaluation was, and the smaller the RMSE was, the better the evaluation was, and the two parameters were parameters for evaluating model prediction indexes.

Figure 10:
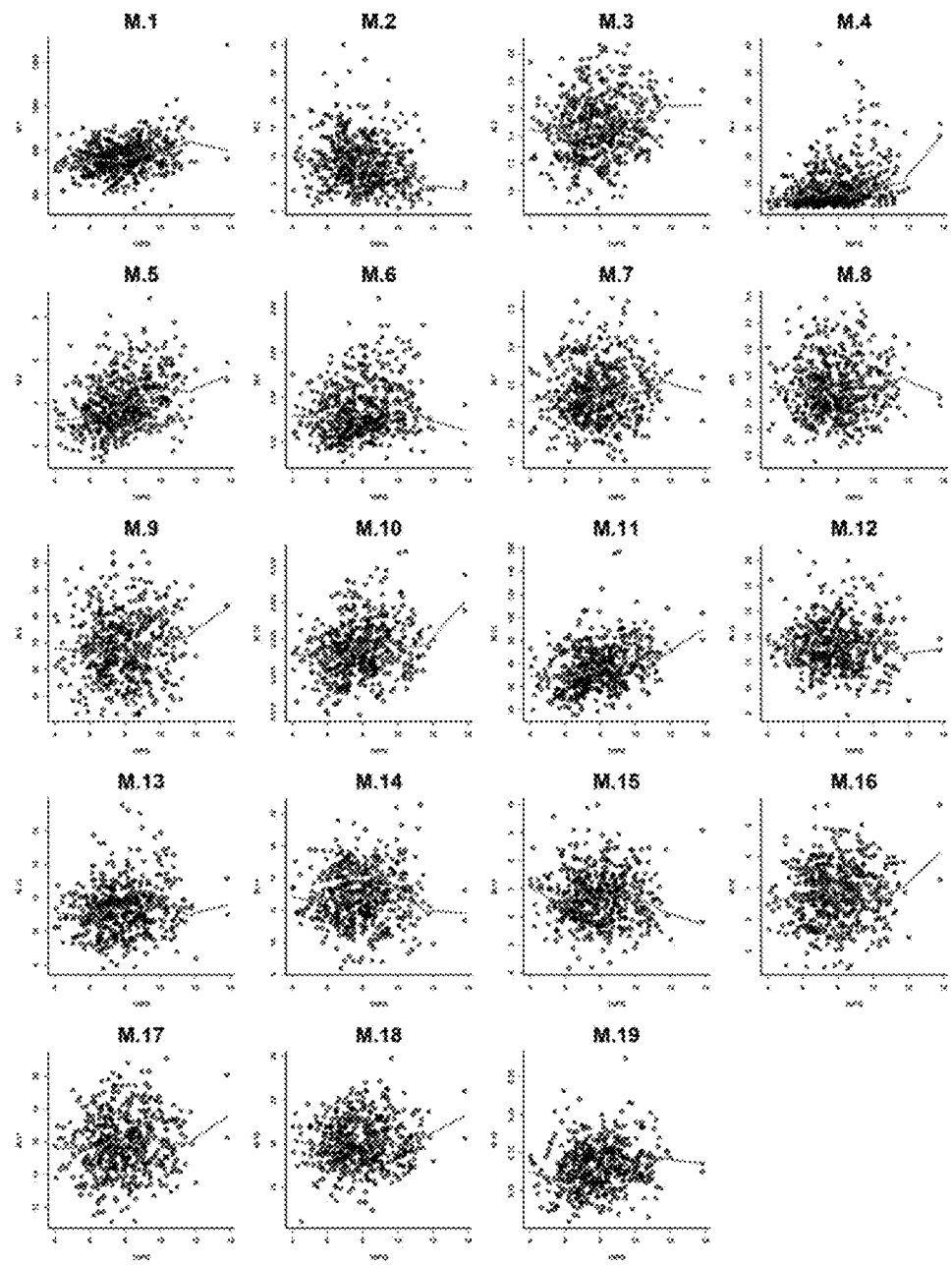
FIG. 10 is a scatter plot and a lowess fitting curve of the 1-hour blood glucose value and the concentration values of 19 markers.
Figure 11:
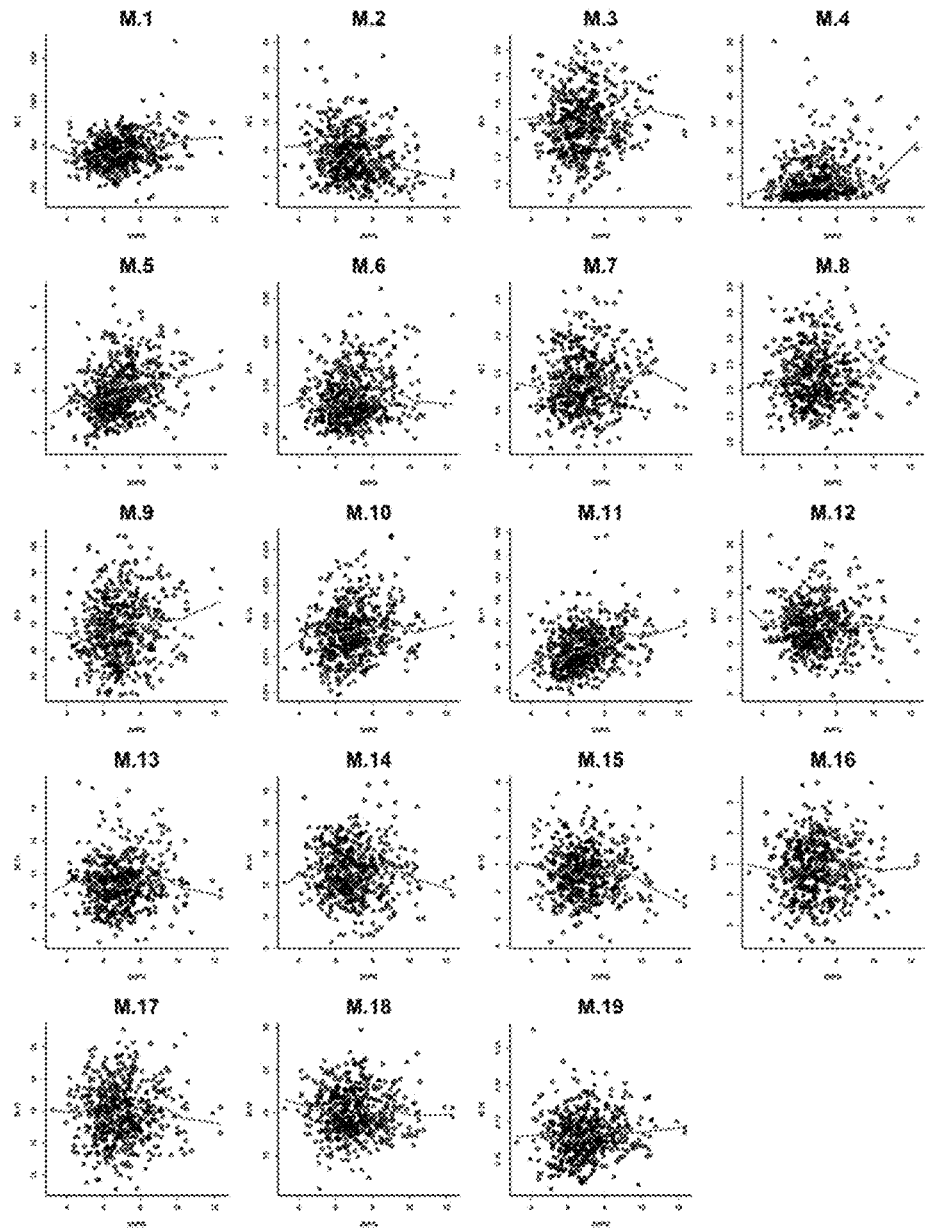
FIG. 11 is a scatter plot and a lowess fitting curve of the 2-hour blood glucose value and the concentration values of 19 markers.

After the trend between the blood glucose level and each independent variable (the serum concentration of the biomarkers) was observed, we think there could be possible nonlinear relationship (shown in FIG. 10 and FIG. 11) between the blood glucose level and the independent variable, and particularly, the polynomial of variables such as M-1, M-2, M-4 and M-11 and the variation trend of dependent variables relatively obviously showed the correlation (lowess fitting curve). So, the adoption of a nonlinear model was considered, such as random forest regression, polynomial regression, support vector regression and gradient boosting regression trees were sequentially tried. Finally, the support vector regression was the best model (shown in Table 9), and the R-squared value was relatively maximum and the RMSE value was relatively minimum. So, the support vector regression model was selected.

TABLE 9

Comparison of fitting effects of nonlinear models

| Module | R-squared | RMSE |
| --- | --- | --- |
| Multiple Linear Regression | 0.32 | 1.32 |
| Random Forest Regression | 0.21 | 1.51 |
| Polynomial regression | 0.22 | 1.22 |
| Gradient boosted regression tree | 0.39 | 1.24 |
| Support Vector Regression | 0.434 | 0.83 |

When the support vector regression model was used to predict the blood glucose level, it was necessary to calculate support vector matrix data of each independent variable such as each biomarker, thereby calculating a weighted value and a coefficient of each biomarker, and using the matrix data to predict a final blood glucose level by a specific calculation prediction model. According to the example, the processes of selecting 19 specific biomarkers to respectively establish a support vector regression model for predicting the blood glucose level at 1 h and 2 h after 0 h under fasting state and optimizing were as follows:

(1) All samples were randomly divided into a training set and a validation set in advance, wherein the training set accounted for 80% of the total sample number, and the validation set accounted for 20%, namely, 398 samples were in the training set, and 101 samples were in the validation set;

(2) A tool used for modeling was R language (Version 3.6.2), an Rstudio operation interface was used, a support vector regression function was from an e1071 software package (Version 1.7.7), a polynomial kernel function (polynomial) was adopted for high-dimensional mapping, and the mathematical expression of the polynomial kernel function was:

$$K(X) = (\gamma \cdot X + coef)^{degree}$$

$$X = \mu_i \cdot v_i$$

where, $\gamma$, coef and degree were parameters to be adjusted; $\mu_i \cdot v_i$ was a linear model of an independent variable; $\|_i$ was the linear coefficient of the $i^{th}$ biomarker; $v_i$, was the serum concentration value of the $i^{th}$ biomarker at 0 h under fasting state. In the example, 19 biomarkers of GDM were selected, i was 1-19 and respectively corresponded to the biomarkers with the serial numbers of M-1 to M-19, as shown in Table 12.

(3) An independent variable matrix (training set) was substituted into an SVR function (K (X)) in a continuous numerical value type, and the variables was respectively the 1 h blood glucose level (1 hPG) and the 2 h blood glucose level (2 hPG), and kernel was set as the polynomial kernel function "polynomial" when the initial parameter was $\gamma=1$, coef=0, degree=1. After modeling, under the condition that the initial parameter was adopted, the R-square values of the polynomial kernel function (polynomial) were 0.43 (1 h) and 0.46 (2 h), and RMSE was 0.83 (1 h) and 0.78 (2 h). The result was not the best result, and the R-square values were smaller than RMSE and were not optimized parameters.

Parameter adjustment adopted a mode of combining grid search and gradient descent, the most possible range of optimal parameters was delimited, and all parameter combinations were traversed in the delimited range. Two finally obtained models respectively contained 469 (1 h) and 454 (2 h) support vectors (support vector matrix (SVRSV)) and variable parameters, the support vectors formed a "space band" in a high-dimensional space, and when a new sample was predicted, the distance between the new sample and the edge of the "space band" was calculated, namely a predicted value.

The equation of a finally obtained support vector regression model was:

$$Y = \sum_{i=1}^{m} W_i \cdot K_i + b$$

where, Y was a predicted blood glucose level (mmol/L), i represented the $i^{th}$ biomarker, m represented the number of biomarkers (m=19), $W_i$ represented the weighted value of the $i^{th}$ biomarker (Table 13), $K_i$ represented the coefficient of the $i^{th}$ biomarker, and b was a constant.

The $K_i$ coefficient was calculated by the following formula to obtain (K(x)):

$$K_i = (\gamma \cdot \mu_i \cdot v_i + coef)^{degree}$$

where, $\gamma$, coef and degree were parameters to be adjusted, $\mu_i \cdot v_i$ was the linear model of the independent variable, i was the linear coefficient of the $i^{th}$ biomarker, and $v_i$ was the detection value ((μg/mL) of the $i^{th}$ biomarker. Parameter related information obtained after optimization was shown in Tables 10 to 13. The RMSE of the support vector regression model under the optimal parameters was 0.67 (1 h) and 0.53 (2 h) respectively.

TABLE 10

| Parameter tuning results of support vector regression modeling | | |
|---|---|---|
| Parameters | 1 hPG | 2 hPG |
| degree | 3 | 3 |
| $\gamma$ | 0.037 | 0.037 |
| coef | 1 | 2 |
| b | 0.0628 | 0.0797 |

TABLE 11

| Modeling test results of support vector regression | | | |
|---|---|---|---|
| | Parameters | R-squared | RMSE |
| 1-h blood glucose level | Training set | 0.67 | 0.67 |
| | Validation set | — | 0.59 |
| 2-h blood glucose level | Training set | 0.68 | 0.53 |
| | Validation set | — | 0.59 |

TABLE 12

Linear coefficients for 19 independent variables

| Serial number | Biomarkers | $\mu_i$ (linear coefficient) | |
|---|---|---|---|
| | | 1 h | 2 h |
| M-1 | glucose | −5.94596E−05 | −0.000356085 |
| M-2 | 1,5-anhydroglucitol (1,5-AG) | −0.026149544 | −0.033072209 |
| M-3 | 3-methyl-2-oxobutyrate | 0.28517657 | 0.35070682 |
| M-4 | 3-hydroxybutyrate (BHBA) | 0.0073573 | −0.003628292 |
| M-5 | 2-hydroxybutyrate (AHB) | 0.265723742 | 0.227143481 |
| M-6 | pantothenic acid | 11.02574829 | 10.14047839 |
| M-7 | 3-methyl-2-oxovalerate | 0.671723153 | 0.684864863 |
| M-8 | 4-methyl-2-oxopentanoate | −0.753129322 | −0.675811046 |
| M-9 | 1-palmitoyl-GPC (16:0) | −0.000533758 | 0.011682708 |
| M-10 | palmitoylcarnitine | 28.73541414 | 3.438905244 |
| M-11 | oleate | 0.009542539 | 0.011565459 |
| M-12 | glycine | 0.023184566 | 0.050289956 |
| M-13 | phenylalanine | 0.066366599 | −0.022181694 |
| M-14 | serine | −0.022813626 | −0.038488107 |
| M-15 | tyrosine | −0.151902626 | −0.175825644 |
| M-16 | isoleucine | 0.053198092 | 0.165291135 |
| M-17 | leucine | 0.051457031 | 0.077198939 |
| M-18 | valine | 0.005974243 | −0.070012174 |
| M-19 | 2-aminoadipic acid | 2.289641593 | 1.889998371 |

TABLE 13

Weighted values for 19 independent variables

| Serial number | Biomarkers | $\mu_i$ (linear coefficient) | |
|---|---|---|---|
| | | 1 h | 2 h |
| M-1 | glucose | −140.1367461 | −98.73331703 |
| M-2 | 1,5-anhydroglucitol (1,5-AG) | −18.20203701 | 3.187643085 |
| M-3 | 3-methyl-2-oxobutyrate | −0.266373135 | −0.21586202 |
| M-4 | 3-hydroxybutyrate (BHBA) | −3.780820943 | −12.36378322 |
| M-5 | 2-hydroxybutyrate (AHB) | 0.703137151 | −2.548963953 |
| M-6 | pantothenic acid | 0.012695848 | −0.290267916 |
| M-7 | 3-methyl-2-oxovalerate | 0.390205074 | 0.192553693 |
| M-8 | 4-methyl-2-oxopentanoate | −0.34291643 | −0.858808125 |
| M-9 | 1-palmitoyl-GPC (16:0) | −8.627272594 | 15.2824188 |
| M-10 | palmitoylcarnitine | 0.012476258 | −0.009794368 |
| M-11 | oleate | 4.889600901 | −17.62280907 |
| M-12 | glycine | −0.140125414 | −6.38707688 |
| M-13 | phenylalanine | −2.270950842 | −5.655502071 |
| M-14 | serine | −3.66914922 | −2.357173357 |
| M-15 | tyrosine | 1.697783174 | −0.809820523 |
| M-16 | isoleucine | −1.961842966 | 1.810651075 |
| M-17 | leucine | −6.56784338 | 0.243270797 |
| M-18 | valine | −4.497375666 | −3.100345313 |
| M-19 | 2-aminoadipic acid | −0.037450268 | −0.150868078 |

Note:
The calculation formula of the weight value: $W_i = SVR_{coef}\% * \% SVR_{sv}$;

SVRcoef was the coefficient of 1 (1 h) and 2 (2 h), SVRsv was the support vector matrix of the SVR model; %*% meant matrix multiplication, the specific value and calculation process were omitted, so as to obtain the weight of the above indicators.

Figure 12:
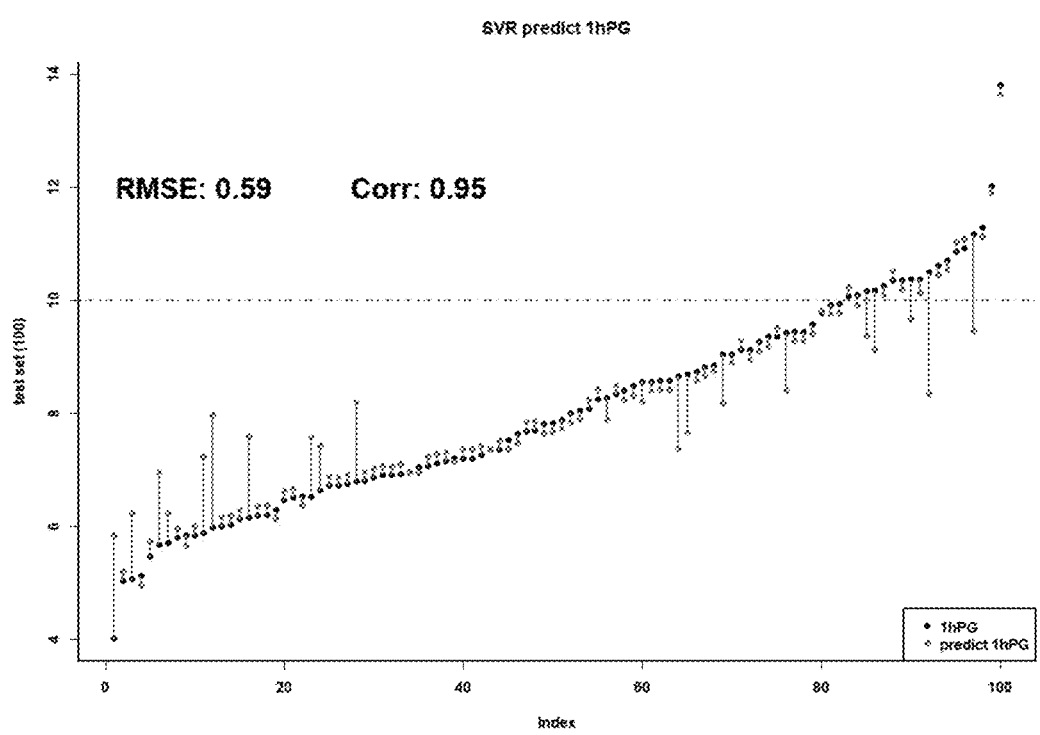
FIG. 12 is a schematic diagram of the prediction of the 1-hour blood glucose value of the validation set by the support vector regression model.
Figure 13:
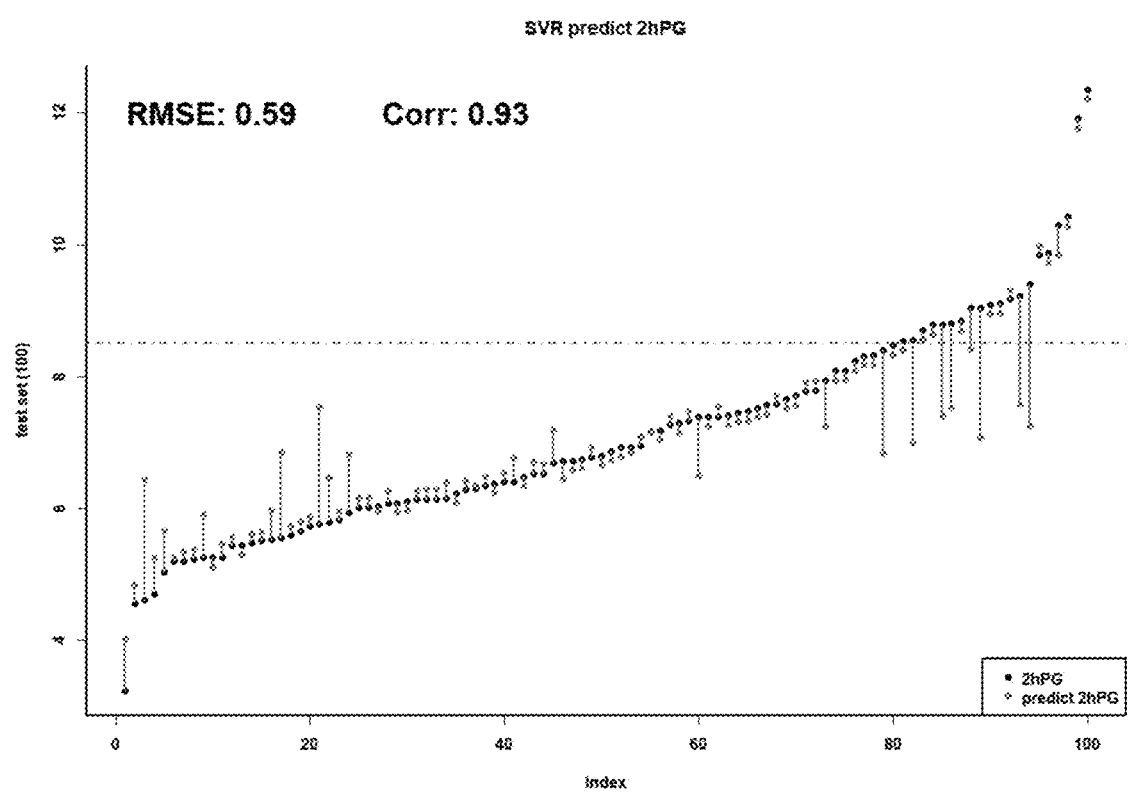
FIG. 13 is a schematic diagram of the prediction of the 2-hour blood glucose value of the validation set by the support vector regression model.

The RMSE of a support vector regression model for predicting the blood glucose level at 1 h after 0 h under fasting state and the RMSE of the support vector regression model for predicting the blood glucose level 2 h after oh under fasting state were respectively 0.67 (1 h) and 0.53 (2 h) and were obtained through final optimization. According to the blood glucose level predicated through the above modes and the blood glucose level actually measured through the above models, the Pearson correlation coefficient of the actual value and the predicted value was 0.95 (1 h) and 0.93 (2 h), and the RMSE was 0.59 (1 h) and 0.59 (2 h). The specific data result and the graphical representation were shown in the FIG. 12 and the FIG. 13, a black point in the figure was an actually measured blood glucose level by OGTT, a gray point was a predicted model value, a gray dotted line was a standard of a clinical diagnosis basis, and the length of a connecting line between the black point and a red point represented the difference between the black point and the red point. The result of predicting validation set samples through the support vector regression model showed that the difference between the predicted blood glucose level and the actually measured blood glucose level of most samples was within an acceptable range, the fitting degree of the training set was highest compared with other methods, the difference between the predicted value and the actually measured value of 86% of samples in the validation set was smaller than 1, the individual difference was large, and the number of the samples influencing the negative and positive results of GDM also conformed to expectation.

It was fully indicated that the blood glucose levels at 1 h and 2 h after 0 h under fasting state could be predicted by adopting the nonlinear regression model of the system and combining the weighted value and the coefficient of the marker and the actually measured concentration of a fasting marker, and whether the pregnant individuals was a diabetic patient or not was judged according to the predicted value, so that the pregnant individuals could be predicted early, and the measurement frequency was reduced. Clinical tests were carried out by utilizing the above models, the blood glucose level predicted by adopting the prediction model of the system was high in correlation with the actually measured value, and the system could be practically applied to clinic.

These embodiments are also included in this invention.
1. A method for confirming a metabolic syndrome in a pregnant subject, wherein the method comprises:
 a) inputting the concentration of a plurality of biomarkers present in a blood sample of one or more pregnant subjects into a support vector regression model;
 b) generating an operation module comprising the support vector regression model, where the operation module is configured to generate a Score for a blood glucose level at n hours after a fasting state has been achieved; and
 c) if the Score exceeds 5.0 then the subject undergoes one or more additional clinical tests to confirm the subject is suffering from a metabolic syndrome selected from the group consisting of diabetes, gestational diabetes and prediabetes.
2. The method according to clause 1, wherein the operational module is generated using a model selected from the group consisting of a Boolean statistical method, a support vector regression, a logistic regression, a least squares regression and a non-Boolean statistical method.
3. The method according to clause 2, wherein the Score is calculated from equation I $$\text{Score} = \sum_{i=1}^{19} W_i \cdot K_i + b \quad \text{equation I}$$

where, i represents the ith biomarker, $W_i$ represents the weighted value of the ith biomarker, b is a constant, and $K_i$ is calculated from equation II:

$$K_i = (\gamma \cdot \mu_i \cdot v_i + \text{coef})^{degree} \quad \text{equation II}$$

where, i is the linear coefficient of the ith biomarker, $v_i$ is the concentration of the ith biomarker, and $\gamma$, coef and degree are adjustable parameters.
4. The method according to clause 3, wherein the subject is pregnant and the metabolic syndrome is gestational diabetes.
5. The method according to clause 3, wherein the biomarkers are: glucose; 1,5-anhydroglucitol; 3-methyl-2-oxobutyrate; 3-hydroxybutyrate; 2-hydroxybutyrate; pantothenic acid; 3-methyl-2-oxovalerate; 4-methyl-2-oxovalerate; palmitoyl-GPC; palmitoylcarnitine; oleic acid; glycine; phenylalanine; serine; tyrosine; isoleucine; leucine; valine; and 2-aminoadipic acid.
6. The method according to clause 4, wherein $W_1, W_2 \ldots W_{19}$ are the weighted values of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, 2-aminoadipic acid.
7. The method according to clause 5, wherein $\mu_1, \mu_2 \ldots \mu_{19}$ are respectively the linear coefficient of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid respectively, wherein $v_1, v_2 \ldots v_{19}$ are the concentrations of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid in the blood samples of the subjects.
8. The method according to clause 1, wherein the sample is isolated from a biological material of the subject.
9. The method according to clause 8, wherein wherein the biological material is a fecal sample of the subject.
10. The method according to clause 8, wherein the biological material is derived from a blood sample of the subject.
11. A method for evaluating whether a subject is at risk of developing a metabolic syndrome, comprising:
 (a) detecting a concentration of a plurality of biomarkers in a sample, wherein the plurality of biomarkers are selected from the group consisting of: glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid; and
 (b) if the sum of the plurality of biomarkers is greater than a cut-off value, the subject is at risk of developing or suffering from a metabolic syndrome, and (c) if the sum of the plurality of biomarkers is less than the cut-off value, the subject is not at risk of developing a metabolic syndrome.

12. The method according to clause 11, wherein the sample is isolated from a biological material of the subject.

13. The method according to clause 12, wherein wherein the biological material is a fecal sample of the subject.

14. The method according to clause 12, wherein the biological material is derived from a blood sample of the subject.

15. The method according to clause 11, wherein the sample is isolated from biological material selected from the group consisting of saliva, urine, tissue, and skin of the subject.

16. The method according to clause 11, wherein the metabolic syndrome is selected from the group consisting of diabetes, gestational diabetes and prediabetes 17. The method according to clause 16, wherein the subject is evaluated as at risk for developing gestational diabetes before the third trimester.

18. The method according to clause 11, further comprising:
    (d) inputting the concentration of the plurality of biomarkers into a support vector regression model; and
    e) generating an operation module comprising the support vector regression model, where the operation module is configured to generate a Score based on the sum of the plurality of biomarkers.

19. The method according to clause 18, wherein the operational module is generated using a model selected from the group consisting of a Boolean statistical method, a support vector regression, a logistic regression, a least squares regression and a non-Boolean statistical method.

20. The method according to clause 18, wherein the Score is calculated from equation I $$\text{Score} = \sum_{i=1}^{19} W_i \cdot K_i + b \qquad \text{equation I}$$

where, i represents the ith biomarker, $W_1, W_2 \ldots W_{19}$ are the weighted values of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, 2-aminoadipic acid, b is a constant, and $K_i$ is calculated from equation II:

$$K_i = (\gamma \cdot \mu_i \cdot v_i + \text{coef})^{degree} \qquad \text{equation II}$$

where, $\mu_1, \mu_2 \ldots \mu_{19}$, the linear coefficient of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid are 3.425, 0.854, −4.598, −1.307, +0.309, −2.253, −0.335, −0.172, −1.273, −0.422, and 0.622 respectively, $v_i$ is the concentration of the ith biomarker, and γ, coef and degree are adjustable parameters.

21. The method according to clause 20, wherein the subject is pregnant and the metabolic syndrome is gestational diabetes.

22. The method according to clause 21, wherein the Score is 0.515.

23. A method for evaluating whether a pregnant subject is at risk of developing gestational diabetes, comprising:
    (a) detecting a concentration of a plurality of biomarkers in a sample, wherein the plurality of biomarkers are selected from the group consisting of: palmitoylcarnitine, oleic acid, glycine, phenylalanine, serine, tyrosine, isoleucine, leucine, valine, and 2-aminoadipic acid; and
    (b) inputting the concentration of the plurality of biomarkers into a support vector regression model;
    c) generating an operation module comprising the support vector regression model, where the operation module is configured to generate a Score based on the sum of the plurality of biomarkers;
    (d) if the sum of the plurality of biomarkers is greater than a cut-off value, the subject is at risk of developing or suffering from gestational diabetes, and
    (e) if the sum of the plurality of biomarkers is less than the cut-off value, the subject is not at risk of developing gestational diabetes.

24. The method according to clause 23, wherein the Score is calculated from equation I $$\text{Score} = \sum_{i=1}^{10} W_i \cdot K_i + b \qquad \text{equation I}$$

where, i represents the ith biomarker, $W_1, W_2 \ldots W_{19}$ are the weighted values of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, 2-aminoadipic acid, b is a constant, and $K_i$ is calculated from equation II:

$$K_i = (\gamma \cdot \mu_i \cdot v_i + \text{coef})^{degree} \qquad \text{equation II}$$

where $\mu_1, \mu_2 \ldots \mu_{19}$, the linear coefficient of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid are 3.425, 0.854, −4.598, −1.307, +0.309, −2.253, −0.335, −0.172, −1.273, −0.422, and 0.622 respectively, $v_i$ is the concentration of the ith biomarker γ, coef and degree are adjustable parameters.

25. The method according to clause 23, wherein the Score is 0.661.

26. A method for evaluating whether a pregnant subject is at risk of developing gestational diabetes, comprising:
    (a) isolating at a time n hours after a previous meal a sample from a pregnant subject;
    (b) performing an assay on the sample to determine an abundance of at least four (4) metabolites present for each subject selected from the group consisting of:
    (i) at least one (1) acyl carnitine metabolite selected from the group consisting of R-3-hydroxybutyrylcarnitine, carnitine, cis-3,4-methyleneheptanoylcarnitine, and palmitoylcarnitine;
    (ii) at least one (1) amino acid selected from the group consisting of: glycine, isoleucine, leucine, phenylalanine, pyroglutamine, serine, tyrosine, and valine;
    (iii) at least one (1) metabolite generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate;
(iv) at least one (1) metabolite selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; and at most one (1) cholate metabolite selected from the group consisting of glycochenodeoxycholate, deoxycholate, glycocholenate sulfate, glycolithocholate sulfate, and isoursodeoxycholate sulfate;
c) selecting at least four (4) biomarkers based on the abundance of the at least four (4) metabolites for each subject; and
(d) inputting the abundance of the at least four (4) biomarkers for each subject into a support vector regression model;
(e) generating an operation module comprising the support vector regression model, to generate a Score for for each subject; and
(f) if the Score exceeds 0.5 then the subject is at risk of developing gestational diabetes and undergoes additional clinical tests to evaluate the risk of gestational diabetes.

27. The method according to clause 26, wherein n equals 6 and the sample is taken after approximately six hours of fasting, where approximately means plus or minus one hour.

28. A method for diagnosing a pregnant subject is at risk of gestational diabetes, comprising:
(a) isolating at a time n hours after a previous meal a sample from a pregnant subject;
(b) performing an assay on the sample to determine an abundance of at least five (5) metabolites present for each subject selected from the group consisting of:
(i) at least one (1) acyl carnitine metabolite selected from the group consisting of R-3-hydroxybutyrylcarnitine, carnitine, cis-3,4-methyleneheptanoylcarnitine, and palmitoylcarnitine;
(ii) at least one (1) amino acid selected from the group consisting of: glycine, isoleucine, leucine, phenylalanine, pyroglutamine, serine, tyrosine, and valine;
(iii) at least one (1) metabolite generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate; and
(iv) at least one (1) metabolite selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate;
c) selecting at least five (5) biomarkers based on the abundance of the at least five (5) metabolites for each subject;
(d) inputting the abundance of the at least five (5) biomarkers for each subject into a support vector regression model;
(e) generating an operation module comprising the support vector regression model, to generate a Score for for each subject; and
(f) if the Score exceeds 0.5 then the subject undergoes additional clinical tests to diagnose the risk of gestational diabetes.

29. The method according to clause 28, wherein n equals 6 and the sample is taken after approximately six hours of fasting, where approximately means plus or minus one hour.

30. The method of clause 28, further comprising if the Score exceeds 0.6 the subject and the fetus are monitored for fetal malformation during pregnancy.

31. A method for diagnosing a pregnant subject is at risk of gestational diabetes, comprising:
(a) isolating at a time n hours after a previous meal a sample from a pregnant subject;
(b) performing an assay on the sample to determine an abundance of at least six (6) metabolites present for each subject selected from the group consisting of:
(i) at least one (1) acyl carnitine metabolite selected from the group consisting of R-3-hydroxybutyrylcarnitine, carnitine, cis-3,4-methyleneheptanoylcarnitine, and palmitoylcarnitine;
(ii) at least one (1) amino acid selected from the group consisting of: glycine, isoleucine, leucine, phenylalanine, pyroglutamine, serine, tyrosine, and valine;
(iii) at least two (2) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate; and
(iv) at least two (2) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate;
c) selecting at least six (6) biomarkers based on the abundance of the at least six (6) metabolites for each subject;
(d) inputting the abundance of the at least six (6) biomarkers for each subject into a support vector regression model;
(e) generating an operation module comprising the support vector regression model, to generate a Score for for each subject; and
(f) if the Score exceeds 0.5 then the subject undergoes additional clinical tests to diagnose the risk of gestational diabetes.

32. The method according to clause 31, wherein n equals 6 and the sample is taken after approximately six hours of fasting, where approximately means plus or minus one hour.

33. The method of clause 31, further comprising if the Score exceeds 0.5 the subject and the fetus are monitored for fetal malformation during pregnancy.

34. A method for diagnosing a pregnant subject is at risk of gestational diabetes, comprising:
(a) isolating at a time n hours after a previous meal a sample from a pregnant subject;
(b) performing an assay on the sample to determine an abundance of at least seven (7) metabolites present for each subject selected from the group consisting of:
(i) at least one (1) acyl carnitine metabolite selected from the group consisting of R-3-hydroxybutyrylcarnitine, carnitine, cis-3,4-methyleneheptanoylcarnitine, and palmitoylcarnitine;

(ii) at least one (1) amino acid selected from the group consisting of: glycine, isoleucine, leucine, phenylalanine, pyroglutamine, serine, tyrosine, and valine;

(iii) at least two (2) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate; and (iv) at least three (3) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate;

c) selecting at least seven (7) biomarkers based on the abundance of the at least seven (7) metabolites for each subject;

(d) inputting the abundance of the at least seven (7) biomarkers for each subject into a support vector regression model;

(e) generating an operation module comprising the support vector regression model, to generate a Score for for each subject; and (f) if the Score exceeds 0.5 then the subject undergoes additional clinical tests to diagnose the risk of gestational diabetes.

35. The method according to clause 34, wherein n equals 6 and the sample is taken after approximately six hours of fasting, where approximately means plus or minus one hour.

36. The method of clause 34, further comprising if the Score exceeds 0.5 the subject and the fetus are monitored for fetal malformation during pregnancy.

37. A method for diagnosing a pregnant subject is at risk of gestational diabetes, comprising:

(a) isolating at a time n hours after a previous meal a sample from a pregnant subject;

(b) performing an assay on the sample to determine an abundance of at least eight (8) metabolites present for each subject selected from the group consisting of:

(i) at least one (1) acyl carnitine metabolite selected from the group consisting of R-3-hydroxybutyrylcarnitine, carnitine, cis-3,4-methyleneheptanoylcarnitine, and palmitoylcarnitine;

(ii) at least one (1) amino acid selected from the group consisting of: glycine, isoleucine, leucine, phenylalanine, pyroglutamine, serine, tyrosine, and valine;

(iii) at least two (2) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate; and (iv) at least four (4) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate;

c) selecting at least eight (8) biomarkers based on the abundance of the at least eight (8) metabolites for each subject;

(d) inputting the abundance of the at least eight (8) biomarkers for each subject into a support vector regression model;

(e) generating an operation module comprising the support vector regression model, to generate a Score for for each subject; and (f) if the Score exceeds 0.5 then the subject undergoes additional clinical tests to diagnose the risk of gestational diabetes.

38. The method according to clause 37, wherein n equals 6 and the sample is taken after approximately six hours of fasting, where approximately means plus or minus one hour.

39. The method of clause 37, further comprising if the Score exceeds 0.5 the subject and the fetus are monitored for fetal malformation during pregnancy.

40. A method for diagnosing a pregnant subject is at risk of gestational diabetes, comprising:

(a) isolating at a time n hours after a previous meal a sample from a pregnant subject;

(b) performing an assay on the sample to determine an abundance of at least nine (9) metabolites present for each subject selected from the group consisting of:

(i) at least five (5) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate; and (iv) at least four (4) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate;

c) selecting at least nine (9) biomarkers based on the abundance of the at least nine (9) metabolites for each subject;

(d) inputting the abundance of the at least nine (9) biomarkers for each subject into a support vector regression model;

(e) generating an operation module comprising the support vector regression model, to generate a Score for for each subject; and (f) if the Score exceeds 0.5 then the subject undergoes additional clinical tests to diagnose the risk of gestational diabetes.

41. The method according to clause 40, wherein n equals 6 and the sample is taken after approximately six hours of fasting, where approximately means plus or minus one hour.

42. The method of clause 40, further comprising if the Score exceeds 0.5 the subject and the fetus are monitored for fetal malformation during pregnancy.

43. A method for diagnosing a pregnant subject is at risk of gestational diabetes, comprising:

(a) isolating at a time n hours after a previous meal a sample from a pregnant subject;

(b) performing an assay on the sample to determine an abundance of at least ten (10) metabolites present for each subject selected from the group consisting of:

(i) at least five (5) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate; and (iv) at least five (5) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate;

c) selecting at least ten (10) biomarkers based on the abundance of the at least ten (10) metabolites for each subject;

d) inputting the abundance of the at least ten (10) biomarkers for each subject into a support vector regression model;

e) generating an operation module comprising the support vector regression model, to generate a Score for for each subject; and f) if the Score exceeds 0.5 then the subject undergoes additional clinical tests to diagnose the risk of gestational diabetes.

44. The method according to clause 43, wherein n equals 6 and the sample is taken after approximately six hours of fasting, where approximately means plus or minus one hour.

45. The method of clause 43, further comprising if the Score exceeds 0.5 the subject and the fetus are monitored for fetal malformation during pregnancy.

Embodiments Contemplated Herein Include Embodiments P1-P43 Following

Embodiment P1. A method for confirming a metabolic condition in a subject, where the method comprises inputting the concentration of a plurality of biomarkers present in a sample of one or more pregnant subjects into a support vector regression model, generating an operation module comprising the support vector regression model, where the operation module is configured to generate a Score for a blood glucose level at n hours after a fasting state has been achieved, and undergoing one or more additional clinical tests to confirm the subject is suffering from a metabolic condition selected from the group consisting of diabetes, gestational diabetes and prediabetes if the Score exceeds 5.0.

Embodiment P2. The method of Embodiment P1, where the operational module is generated using a model selected from the group consisting of a Boolean statistical method, a support vector regression, a logistic regression, a least squares regression and a non-Boolean statistical method.

Embodiment P3. The method of Embodiment P2, where the Score is calculated from equation I, $$\text{Score} = \sum_{i=1}^{19} W_i \cdot K_i + b, \quad \text{equation I}$$

where, i represents the i-th biomarker, $W_i$ represents the weighted value of the i-th biomarker, b is a constant, and $K_i$ is calculated from equation II, $K_i = (\gamma \cdot \mu_i \cdot v_i + \text{coef})^{degree}$ equation II, where, i is the linear coefficient of the i-th biomarker, $v_i$ is the concentration of the i-th biomarker, and γ, coef and degree are adjustable parameters.

Embodiment P4. The method of any one of Embodiments P1 to P3, where the subject is pregnant and the metabolic condition is gestational diabetes.

Embodiment P5. The method of any one of Embodiments P1 to P4, where the biomarkers are: glucose; 1,5-anhydroglucitol; 3-methyl-2-oxobutyrate; 3-hydroxybutyrate; 2-hydroxybutyrate; pantothenic acid; 3-methyl-2-oxovalerate; 4-methyl-2-oxovalerate; palmitoyl-GPC; palmitoylcarnitine; oleic acid; glycine; phenylalanine; serine; tyrosine; isoleucine; leucine; valine; and 2-aminoadipic acid.

Embodiment P6. The method of any one of Embodiments P3 to P5, where $W_1, W_2 \ldots W_{19}$ are the weighted values of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, 2-aminoadipic acid.

Embodiment P7. The method of any one of Embodiments P3 to P6, where $\mu_1, \mu_2 \ldots \mu_{19}$ are respectively the linear coefficient of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid respectively, where $v_1, v_2 \ldots v_{19}$ are the concentrations of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid in the sample of the subject.

Embodiment P8. The method of any one of Embodiments P1 to P7, where the sample is isolated from a biological material of the subject.

Embodiment P9. The method of any one of Embodiments P1 to P8, where the biological material is a fecal sample of the subject.

Embodiment P10. The method of any one of Embodiments P1 to P8, where the biological material is derived from a blood sample of the subject.

Embodiment P11. A method for evaluating whether a subject is at risk of developing a metabolic condition, comprising detecting a concentration of a plurality of biomarkers in a sample, where the plurality of biomarkers are selected from the group consisting of: glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid; and, if the sum of the plurality of biomarkers is greater than a cut-off value, the subject is at risk of developing or suffering from a metabolic condition, and if the sum of the plurality of biomarkers is less than the cut-off value, the subject is not at risk of developing a metabolic condition.

Embodiment P12. The method of Embodiment P11, where the sample is isolated from a biological material of the subject.

Embodiment P13. The method of Embodiment P12, where the biological material is a fecal sample of the subject.

Embodiment P14. The method of Embodiment P12, where the biological material is derived from a blood sample of the subject.

Embodiment P15. The method of Embodiment P12, where the sample is isolated from biological material selected from the group consisting of saliva, urine, tissue, and skin of the subject.

Embodiment P16. The method of Embodiments P11 to P15, where the metabolic condition is selected from the group consisting of diabetes, gestational diabetes and pre-diabetes.

Embodiment P17. The method of Embodiments P11 to P16, where the subject is evaluated as at risk for developing gestational diabetes before the third trimester.

Embodiment P18. The method of Embodiments P11 to P17, further comprising inputting the concentration of the plurality of biomarkers into a support vector regression model, and generating an operation module comprising the support vector regression model, where the operation module is configured to generate a Score based on the sum of the plurality of biomarkers.

Embodiment P19. The method of Embodiments P11 to P18, where the operational module is generated using a model selected from the group consisting of a Boolean statistical method, a support vector regression, a logistic regression, a least squares regression and a non-Boolean statistical method.

Embodiment P20. The method of Embodiments P11 to P19, where the Score is calculated from equation I, $$\text{Score} = \sum_{i=1}^{19} W_i \cdot K_i + b, \quad \text{equation I}$$

where, i represents the i-th biomarker, $W_1, W_2 \ldots W_{19}$ are the weighted values of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, 2-aminoadipic acid, b is a constant, and $K_i$ is calculated from equation II, $K_1 = (\gamma \cdot \mu_i \cdot v_i + \text{coef})^{degree}$, equation II, where, $\mu_1, \mu_2 \ldots \mu_{19}$, the linear coefficient of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid are 3.425, 0.854, −4.598, −1.307, +0.309, −2.253, −0.335, −0.172, −1.273, −0.422, and 0.622 respectively, $v_i$ is the concentration of the i-th biomarker, and γ, coef and degree are adjustable parameters.

Embodiment P21. The method of Embodiments P11 to P20, where the subject is pregnant and the metabolic condition is gestational diabetes.

Embodiment P22. The method of Embodiments P11 to P21, where the Score is 0.515.

Embodiment P23. A method for evaluating whether a pregnant subject is at risk of developing gestational diabetes, comprising detecting a concentration of a plurality of biomarkers in a sample, where the plurality of biomarkers are selected from the group consisting of: palmitoylcarnitine, oleic acid, glycine, phenylalanine, serine, tyrosine, isoleucine, leucine, valine, and 2-aminoadipic acid, and inputting the concentration of the plurality of biomarkers into a support vector regression model, generating an operation module comprising the support vector regression model, where the operation module is configured to generate a Score based on the sum of the plurality of biomarkers, if the sum of the plurality of biomarkers is greater than a cut-off value, the subject is at risk of developing or suffering from gestational diabetes, and if the sum of the plurality of biomarkers is less than the cut-off value, the subject is not at risk of developing gestational diabetes.

Embodiment P24. The method of Embodiment P23, where the Score is calculated from equation I, $$\text{Score} = \sum_{i=1}^{10} W_i \cdot K_i + b, \quad \text{equation I}$$

where, i represents the i-th biomarker, $W_1, W_2 \ldots W_{19}$ are the weighted values of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, 2-aminoadipic acid, b is a constant, and $K_i$ is calculated from equation II, $K_1 = (\gamma \cdot \mu_i \cdot v_i + \text{coef})^{degree}$, equation II, where $\mu_1, \mu_2 \ldots \mu_{19}$, the linear coefficient of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleic acid, glycine, phenylalanine, serine, tyrosine, isoleucine, leucine, valine, and 2-aminoadipic acid are 3.425, 0.854, −4.598, −1.307, +0.309, −2.253, −0.335, −0.172, −1.273, −0.422, and 0.622 respectively, $v_i$ is the concentration of the i-th biomarker γ, coef and degree are adjustable parameters.

Embodiment P25. The method of Embodiment P24, where the Score is 0.661.

Embodiment P26. A method for evaluating whether a pregnant subject is at risk of developing gestational diabetes, comprising, isolating at a time n hours after a previous meal a sample from a pregnant subject, performing an assay on the sample to determine an abundance of at least four (4) metabolites present for each subject selected from the group consisting of at least one (1) acyl carnitine metabolite selected from the group consisting of R-3-hydroxybutyryl-carnitine, carnitine, cis-3,4-methyleneheptanoylcarnitine, and palmitoylcarnitine, at least one (1) amino acid selected from the group consisting of: glycine, isoleucine, leucine, phenylalanine, pyroglutamine, serine, tyrosine, and valine, at least one (1) metabolite generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate, at least one (1) metabolite selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate, and at most one (1) cholate metabolite selected from the group consisting of glycochenodeoxycholate, deoxycholate, glycocholenate sulfate, glycolithocholate sulfate, and isoursodeoxycholate sulfate, selecting at least four (4) biomarkers based on the abundance of the at least four (4) metabolites for each subject, and inputting the abundance of the at least four (4) biomarkers for each subject into a support vector regression model, generating an operation module comprising the support vector regression model, to generate a Score for each subject; and undergoing one or more additional clinical tests to confirm the subject is suffering from gestational diabetes and/or diabetes if the Score exceeds 5.0.

Embodiment P27. The method of Embodiment P26, where n equals 6 and the sample is taken after approximately six hours of fasting, where approximately means plus or minus one hour.

Embodiment P28. A method for diagnosing a pregnant subject is at risk of gestational diabetes, comprising, isolating at a time n hours after a previous meal a sample from a pregnant subject, performing an assay on the sample to determine an abundance of at least five (5) metabolites present for each subject selected from the group consisting of at least one (1) acyl carnitine metabolite selected from the group consisting of R-3-hydroxybutyrylcarnitine, carnitine, cis-3,4-methyleneheptanoylcarnitine, and palmitoylcarnitine, at least one (1) amino acid selected from the group consisting of: glycine, isoleucine, leucine, phenylalanine, pyroglutamine, serine, tyrosine, and valine, at least one (1) metabolite generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, 7-glutamyl-epsilon-lysine, N6-acetyllysine, histidylalanine, threonate, N-acetyltaurine, N-acetyltryptophan, N-acetylvaline, and isovalerate, and at least one (1) metabolite selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate, selecting at least five (5) biomarkers based on the abundance of the at least five (5) metabolites for each subject, inputting the abundance of the at least five (5) biomarkers for each subject into a support vector regression model, generating an operation module comprising the support vector regression model, to generate a Score for each subject, and undergoing one or more additional clinical tests to diagnose the risk of gestational diabetes and/or diabetes if the Score exceeds 5.0.

Embodiment P29. The method of Embodiment P28, where n equals 6 and the sample is taken after approximately six hours of fasting, where approximately means plus or minus one hour.

Embodiment P30. The method of Embodiment P28, further comprising if the Score exceeds 0.6 the subject and the fetus are monitored for fetal malformation during pregnancy.

Embodiment P31. A method for diagnosing a pregnant subject is at risk of gestational diabetes, comprising, isolating at a time n hours after a previous meal a sample from a pregnant subject, performing an assay on the sample to determine an abundance of, at least six (6) metabolites present for each subject selected from the group consisting of at least one (1) acyl carnitine metabolite selected from the group consisting of R-3-hydroxybutyrylcarnitine, carnitine, cis-3,4-methyleneheptanoylcarnitine, and palmitoylcarnitine, at least one (1) amino acid selected from the group consisting of: glycine, isoleucine, leucine, phenylalanine, pyroglutamine, serine, tyrosine, and valine, at least two (2) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate, and at least two (2) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate, selecting at least six (6) biomarkers based on the abundance of the at least six (6) metabolites for each subject, inputting the abundance of the at least six (6) biomarkers for each subject into a support vector regression model, generating an operation module comprising the support vector regression model, to generate a Score for each subject, and undergoing one or more additional clinical tests to confirm the subject is suffering from gestational diabetes and/or diabetes if the Score exceeds 5.0.

Embodiment P32. The method of Embodiment P31, where n equals 6 and the sample is taken after approximately six hours of fasting, where approximately means plus or minus one hour.

Embodiment P33. The method of Embodiment P31, further comprising if the Score exceeds 0.5 the subject and the fetus are monitored for fetal malformation during pregnancy.

Embodiment P34. A method for diagnosing a pregnant subject is at risk of gestational diabetes, comprising, isolating at a time n hours after a previous meal a sample from a pregnant subject, performing an assay on the sample to determine an abundance of at least seven (7) metabolites present for each subject selected from the group consisting of, at least one (1) acyl carnitine metabolite selected from the group consisting of R-3-hydroxybutyrylcarnitine, carnitine, cis-3,4-methyleneheptanoylcarnitine, and palmitoylcarnitine, at least one (1) amino acid selected from the group consisting of: glycine, isoleucine, leucine, phenylalanine, pyroglutamine, serine, tyrosine, and valine, at least two (2) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate, and at least three (3) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate, selecting at least seven (7) biomarkers based on the abundance of the at least seven (7) metabolites for each subject, inputting the abundance of the at least seven (7) biomarkers for each subject into a support vector regression model, generating an operation module comprising the support vector regression model, to generate a Score for each subject, and undergoing one or more additional clinical tests to diagnose the risk of gestational diabetes and/or diabetes if the Score exceeds 5.0.

Embodiment P35. The method of Embodiment P34, where n equals 6 and the sample is taken after approximately six hours of fasting, where approximately means plus or minus one hour.

Embodiment P36. The method of Embodiment P34, further comprising if the Score exceeds 0.5 the subject and the fetus are monitored for fetal malformation during pregnancy.

Embodiment P37. A method for diagnosing a pregnant subject is at risk of gestational diabetes, comprising, isolating at a time n hours after a previous meal a sample from a pregnant subject, performing an assay on the sample to determine an abundance of at least eight (8) metabolites present for each subject selected from the group consisting of, at least one (1) acyl carnitine metabolite selected from the group consisting of R-3-hydroxybutyrylcarnitine, carnitine, cis-3,4-methyleneheptanoylcarnitine, and palmitoylcarnitine, at least one (1) amino acid selected from the group consisting of: glycine, isoleucine, leucine, phenylalanine, pyroglutamine, serine, tyrosine, and valine, at least two (2) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate, and at least four (4) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate, selecting at least eight (8) biomarkers based on the abundance of the at least eight (8) metabolites for each subject, inputting the abundance of the at least eight (8) biomarkers for each subject into a support vector regression model, generating an operation module comprising the support vector regression model, to generate a Score for each subject, and undergoing one or more additional clinical tests to diagnose the risk of gestational diabetes and/or diabetes if the Score exceeds 5.0.

Embodiment P38. The method of Embodiment P37, where n equals 6 and the sample is taken after approximately six hours of fasting, where approximately means plus or minus one hour.

Embodiment P39. The method of Embodiment P38, further comprising if the Score exceeds 0.5 the subject and the fetus are monitored for fetal malformation during pregnancy.

Embodiment P40. A method for diagnosing a pregnant subject is at risk of gestational diabetes, comprising, isolating at a time n hours after a previous meal a sample from a pregnant subject, performing an assay on the sample to determine an abundance of at least nine (9) metabolites present for each subject selected from the group consisting of, at least five (5) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate, and at least four (4) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate, selecting at least nine (9) biomarkers based on the abundance of the at least nine (9) metabolites for each subject, inputting the abundance of the at least nine (9) biomarkers for each subject into a support vector regression model, generating an operation module comprising the support vector regression model, to generate a Score for each subject, and undergoing one or more additional clinical tests to diagnose the risk of gestational diabetes and/or diabetes if the Score exceeds 5.0.

Embodiment P41. The method of Embodiment P40, where n equals 6 and the sample is taken after approximately six hours of fasting, where approximately means plus or minus one hour.

Embodiment P42. The method of Embodiment P40, further comprising if the Score exceeds 0.5 the subject and the fetus are monitored for fetal malformation during pregnancy.

Embodiment P43. A method for diagnosing a pregnant subject is at risk of gestational diabetes, comprising, isolating at a time n hours after a previous meal a sample from a pregnant subject, performing an assay on the sample to determine an abundance of at least ten (10) metabolites present for each subject selected from the group consisting of, at least five (5) metabolites generated from an amino acid selected from the group consisting of N-carbamoylalanine, 2-hydroxybutyrate, 3-methyl-2-oxobutyrate, 3-methyl-2-oxovalerate, 4-methyl-2-oxovalerate, γ-glutamyl-epsilon-lysine, N6-acetyllysine, histidylalanine, threonate, N-acetyltaurine, N-acetyltryptophan, N-acetylvaline, and isovalerate, and at least five (5) metabolites selected from the group consisting of 3-(4-hydroxyphenyl)lactate, 3-hydroxybutyrate, 8-methoxykynurenate glucose, and 1,5-anhydroglucitol, glycerophosphoinositol, oleic acid, orotidine, oxalate, pantothenic acid, and indolelactate; glycochenodeoxycholate, deoxycholate, glycocholenate sulfate, glycolithocholate sulfate, and isoursodeoxycholate sulfate, selecting at least ten (10) biomarkers based on the abundance of the at least ten (10) metabolites for each subject, inputting the abundance of the at least ten (10) biomarkers for each subject into a support vector regression model, generating an operation module comprising the support vector regression model, to generate a Score for each subject, and undergoing one or more additional clinical tests to diagnose the risk of gestational diabetes and/or diabetes if the Score exceeds 5.0.

Embodiment P44. The method of Embodiment P43, where n equals 6 and the sample is taken after approximately six hours of fasting, where approximately means plus or minus one hour.

Embodiment P45. The method of Embodiment P43, further comprising if the Score exceeds 0.5 the subject and the fetus are monitored for fetal malformation during pregnancy.

Abbreviations: APCI=atmospheric pressure chemical ionization; APPI=atmospheric pressure photoionization; AUC=area under curve; DHEA-S=dehydroisoandrosterone sulfate; ESI=electrospray ionization; FID=flame ionization detector; FPG=fasting plasma glucose; GDM=gestational diabetes mellitus; $HbA_{1c}$=glycated hemoglobin; h=hour; HESI=heated electrospray ionization; HIRMS—high resolution mass spectrometry; LC=liquid chromatography; MALDI=matrix-assisted laser desorption ionization; OGTT=oral glucose tolerance test; ROC=receiver operating characteristic curve; RPG=random plasma glucose; UHPLC=ultra high performance LC.

The invention claimed is:

1. A system for predicting a blood glucose level of a pregnant individual, wherein the system comprises an operation module, and the operation model comprises a support vector regression model, and the system is configured to predict the blood glucose level at 1 hour after taking oral glucose under a fasting state by using concentrations of biomarkers in blood samples of the pregnant individual under the fasting state and the support vector regression model;

wherein the equation of the support vector regression model is:

$$Y = \sum_{i=1}^{m} W_i \cdot K_i + b$$

where, Y is the predicted blood glucose level, i represents the ith biomarker, m represents a number of the biomarkers, $W_i$ represents a weight of the ith biomarker, $K_i$ represents a coefficient of the ith biomarker, and b is a constant;

wherein $K_i$ is calculated by the following formula:

$$K_i = (\gamma \cdot \mu_i \cdot v_i + \text{coef})^{\text{degree}}$$

where, $\gamma$, coef and degree are parameters to be adjusted, $u_i \cdot v_i$ is a linear model of independent variables, i is a linear coefficient of the ith biomarker, and $v_i$ is the concentration of the ith biomarker;

wherein m is 19;

wherein the biomarkers are glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl glycerol phosphatidylcholine (palmitoyl-GPC), palmitoylcarnitine, oleate, glycine, phenylalanine, serine, tyrosine, isoleucine, leucine, valine, and 2-aminoadipic acid.

2. The system according to claim 1, wherein $W_1, W_2 \ldots W_{19}$ are the weights of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleate, glycine, phenylalanine, serine, tyrosine, isoleucine, leucine, valine, and 2-aminoadipic acid; $\mu_1, \mu_2 \ldots \mu_{19}$ are respectively the weights of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleate, glycine, phenylalanine, serine, tyrosine, isoleucine, leucine, valine, and 2-aminoadipic acid respectively.

3. The system according to claim 2, wherein $v_1, v_2 \ldots v_{19}$ are the concentrations of glucose, 1,5-anhydroglucitol, 3-methyl-2-oxobutyrate, 3-hydroxybutyrate, 2-hydroxybutyrate, pantothenic acid, 3-methyl-2-oxovalerate, 4-methyl-2-oxovalerate, palmitoyl-GPC, palmitoylcarnitine, oleate, glycine, phenylalanine, serine, tyrosine, isoleucine, leucine, valine, and 2-aminoadipic acid in a serum of, the individuals.

4. The system according to claim 3, wherein the concentration is the serum concentration of a biomarker of the individuals at 0 h after fasting.

5. The system according to claim 4, wherein when the support vector regression model is used to predict the blood glucose level at 1 h after taking the oral glucose at 0 h under the fasting state, b=0.0628, $\gamma$=0.037, coef=1, degree=3, $W_1, W_2 \ldots W_{19}$ values are respectively: −140.1367461, −18.20203701, −0.266373135, −3.780820943, 0.703137151, 0.012695848, 0.390205074, −0.34291643, −8.627272594, 0.012476258, 4.889600901, −0.140125414, −2.270950842, −3.66914922, 1.697783174, −1.961842966, −6.56784338, −4.497375666, −0.037450268, $\mu_1, \mu_2 \ldots \mu_{19}$ values are respectively: −5.94596E-05, −0.026149544, 0.28517657, 0.0073573, 0.265723742, 11.02574829, 0.671723153, −0.753129322, −0.000533758, 28.73541414, 0.009542539, 0.023184566, 0.066366599, −0.022813626, −0.151902626, 0.053198092, 0.051457031, 0.005974243, 2.289641593.

* * * * *